United States Patent [19]
Braiman et al.

[11] Patent Number: 5,355,425
[45] Date of Patent: Oct. 11, 1994

[54] LIGHT COUPLING DEVICE FOR OPTICAL FIBERS

[76] Inventors: Mark S. Braiman, 1618 Shady Grove Ct., Charlottesville, Va. 22902-7218; Roy E. Jonas, 417 Brandon Ave., Apartment 1, Charlottesville, Va. 22903

[21] Appl. No.: 940,647

[22] Filed: Sep. 4, 1992

[51] Int. Cl.⁵ ............................................. G02B 6/26
[52] U.S. Cl. .................................... 385/31; 385/34; 385/12; 385/93
[58] Field of Search .................... 385/31, 33, 34, 38, 385/12, 88, 92–94, 39

[56] References Cited

U.S. PATENT DOCUMENTS

| | | | |
|---|---|---|---|
| 4,033,118 | 7/1977 | Powell | 60/641 |
| 4,170,997 | 10/1979 | Pinnow | 128/395 |
| 4,233,493 | 11/1980 | Nath | 219/354 |
| 4,589,729 | 5/1986 | Bridges et al. | 350/96.32 |
| 4,733,933 | 3/1988 | Pikulski | 385/39 |
| 4,737,011 | 4/1988 | Iri et al. | 350/96.2 |
| 4,784,454 | 11/1988 | Dyott | 350/96.20 |
| 4,842,360 | 6/1989 | Caro et al. | 350/96.18 |
| 4,907,883 | 3/1990 | Allmon et al. | 356/317 |
| 4,910,403 | 3/1990 | Kilham et al. | 250/343 |
| 4,920,261 | 4/1990 | Bock et al. | 385/12 |
| 4,979,797 | 12/1990 | Nemeth | 385/12 |
| 5,076,660 | 12/1991 | Messinger | 385/119 |

OTHER PUBLICATIONS

Simhoney et al., Evanescent inoue infrared spectroscopy of liquids using silver halide optical fibers, J. Appl. Physics, vol. 64, 3732–3724 Oct. 1988.

*Primary Examiner*—Rodney B. Bovernick
*Assistant Examiner*—John Ngo
*Attorney, Agent, or Firm*—Sheldon H. Parker

[57] ABSTRACT

A light source to optical fiber coupling device comprising: a diamond coupler, a light source located at an end of the diamond coupler, an optical fiber having an end which is adjacent the other end of the diamond coupler, the optical fiber being in optical coupling relation with the diamond coupler.

35 Claims, 15 Drawing Sheets

LIGHT COUPLING DEVICE FOR OPTICAL FIBERS

BACKGROUND OF THE INVENTION:

1. Field of the Invention

The invention relates to the coupling of optical fibers to a light source, through the use of a diamond coupler.

2. Description of the Prior Art

The use of infrared-transmitting optical fibers as internal reflection elements (IREs) for evanescent-wave absorption spectroscopy has been disclosed in the prior art such as, E. Margalit et al, 1987, Proc. SPIE, Vol. 1048, 145–152; Simhony et al, 1988, J. Appl. Physics, Vol. 64, 3732–3724; D. A. C. Compton et al, 1988, Appl. Spectrosc. Vol. 42, 927–979; J. Heo et al, 1991, Applied Optics, Vol. 30, 3944–3951). Fibers made of silver halide, metal fluorides, chalcogenides, and other materials have been successfully used in the prior art for such measurements in combination with broadband illumination from an incandescent or black-body source focused by means of mirrors and/or lenses onto the end of the fiber. This approach has several disadvantages. First, it can be difficult to adjust the position of a lens or mirror properly to align an invisible IR beam on the end of a narrow fiber. This alignment, once achieved, is likely to be very sensitive to external stresses (mechanical, thermal, etc.). Another disadvantage is that substantial reflective loss occurs when light is incident from air, with a refractive index of 1.0, onto the end of the fiber, which typically has an index of refraction between 1.5 and 3.

Antireflection coatings for chalcogenide fibers have recently become available, however they are generally expensive to design and manufacture and somewhat limited in bandwidth.

The most severe limitation of focusing optics operating in air, however, is the relatively small range of optical fiber modes that can be excited. This limits the amount and kind of light energy available for evanescent-wave spectroscopic measurements. Chalcogenide fibers ranging from 50 to 500 micron in diameter, have been used to obtain evanescent-wave absorption spectra of biological samples. The large diameter of typical infrared-transmitting fibers, relative to the light wavelengths they transmit, is calculated to allow the propagation of a large number of transverse optical modes. However, the difference in refractive index between air and the denser optical fiber materials makes it impossible to excite the full range of allowed transverse modes. In particular, this can make it difficult to transmit into the fiber light rays which propagate near the critical angle for total internal reflection.

The full cone of allowed rays cannot be coupled into an optical fiber by means of an optical element which focuses light from a source through air, onto the fiber end. With this type of conventional illumination, the half-angle of the cone of light rays incident on the fiber end is limited by the aperture of the focusing lens or mirror situated between the source and fiber; typical $f/1$ optics have a half-angle of only 30°. Even more limiting, however, is the reduction in the spread of this cone of rays upon entry into the fiber, which is a result of refraction at the air-fiber interface. The refraction is quite severe for typical chalcogenide fibers, which have indices of refraction in the range 2.4–2.8. Even with an ideal focusing device with an infinite diameter, the greatest possible numerical aperture (N.A.) would be 1, and the half-angle of the cone of rays propagating within the fiber would be limited to 21°. For $f/1$ focusing optics, the N.A. is 0.5 and the cone rays within the fiber has a half-angle of only 10.3°.

Even for a focusing device with an infinite diameter, which is physically unrealizable, the maximum incidence angle on the end of the fiber is 90° and the resulting half-angle of the cone of rays propagating within the fiber is 21°. Another way of stating this limitation is: the numerical aperture of any focusing device operating in air or vacuum is less than 1. This limitation holds quite generally for any type of focusing arrangement, as long as light passes through air ($n=1.0$) for any significant distance between the source and a high-refractive index fiber. In fact, however, infrared optical fibers are themselves calculated to have numerical apertures greater than 1. For example, a commercially-available As-Se-Te fiber has an index of refraction of 2.8 and a numerical aperture calculated to be 2.48. Thus, a focusing optic operating in air is incapable of filling the theoretical aperture of the fiber.

It is obvious from prior art that a focusing optic is entirely superfluous if the source is large enough and/or close enough to the fiber to occupy a full $2\pi$ stearadians of solid angle, as viewed from every point on the end of the fiber. It is also obvious that this might be achieved with a source as small as the cross-sectional area of the fiber, if the source were in direct contact with the end of the fiber. However, coupling broadband light into a fiber by direct optical contact with a blackbody source at a temperature above 1000K has not been pursued previously. Among other reasons, this is because optical fiber materials have low melting points. For example, the softening temperature of typical chalcogenide glasses useful for infrared transmission is about 440K, while a broadband infrared source useful for vibrational spectroscopy must generally operate at 1100–1600K. Thus, a thermally-insulating air space has always been required for transmitting light from a source into the fiber without destroying the latter. This air space is required also if a focusing element is present, since the hot source would also damage optical materials that are currently used for infrared lenses or mirrors.

In previously published descriptions of medical laser instruments for transmitting infrared laser energy to a selected part of the body (see A. L. Gentile and D. A. Pinnow, 1979, U.S. Pat. No. 4,170,997; M. Seal and W. J. P. van Enckevort, 1988, Proc. SPIE, Vol. 969, 144–152), a diamond window has been used on the output end of an optical fiber, i.e. distal from the light source. In this use, the diamond has served as an inert window to protect living tissues from contact with a metal halide optical fiber. However, the ability of diamond to withstand high temperature gradients was not mentioned, nor was the diamond envisioned as being used to increase the range of optical modes which are transmitted either into or out of the fiber.

As developed for temperature sensing systems (see D. C. Tran et al., 1987, Proc. SPIE, Vol. 843, 148–154; S. O. Heinemann et al, 1991, U.S. Pat. No. 4,988,212), prior art has involved the use of a polished sapphire rod to couple radiation emitted by a hot object to an optical fiber bundle. However, sapphire does not have as extensive a spectral wavelength transmission range as diamond and its index of refraction is lower (1.7 compared 2.8 for a diamond). Furthermore, the optical arrangement envisioned in this prior work would not be capable of transmitting high-order optical modes into the fiber, since air, a low refractive-index medium, intervened between the hot source and the input end of the sapphire rod.

Additionally, economic and transparency considerations limit the size of a useful diamond rod coupler to <2 cm, and it is not obvious from the prior work with large sapphire rods that such a short rod could constitute a suitable coupler. This is because the end of the rod that is in contact with the fiber must be kept near room temperature, while the other end will reach a temperature of 1000–1800K. The resulting extreme thermal gradient might be expected to shatter such a short rod of solid material. Thus, the idea of using a short rod of diamond, and cooling its junction to a fiber or fiber bundle while maintaining a temperature differential of up to ~1500° C. across its length, was not obvious from prior art.

Infrared evanescent-wave spectra have previously been obtained using plastic-coated fibers, but only for sample molecules capable of diffusing or dissolving into the coating material until the sample molecules were within several microns of the core fiber material (see V. Ruddy et al., 1990, Appl. Spectros., Vol. 44, 1461–1463). All other previous evanescent wave spectroscopy using chalcogenide optical fibers as IREs has required that the chalcogenide material be directly in contact with the bulk sample. That is, the protective plastic coating had to be removed over at least the measuring portion of the fiber length. This was because only a limited range of transverse modes was present in the fiber, and all of these modes would have been totally reflected at an interface between chalcogenide fiber, having an index of refraction above 2.4, and plastic, with an index of refraction under 1.6. One method for utilizing high-order modes for evanescent-wave spectroscopy has been described previously, involving the use of tapered fibers (see A. Bornstein et al., 1991, Proc. SPIE, Vol. 1591, 256–262; R. D. Driver et al., 1991, Proc. SPIE, Vol. 1591, 168–179). However, this work did not envision making use of these high-order modes for evanescent-wave spectroscopy with fibers that had a thick (>10 micron) lower-refractive-index coating on them. Specifically, it has not been envisioned to use the high-order modes transmitted through tapered fibers for evanescent-wave spectroscopy where the sample contacts only a plastic coating on a chalcogenide fiber.

The instant disclosure provides a direct contact optical coupling for chalcogenide fibers and hot sources through use of a diamond rod as an intermediate medium, thereby overcoming the problems of the prior art.

SUMMARY OF THE INVENTION

A light source to optical fiber coupling device includes a light source, a diamond coupler and an optical fiber or fibers. The diamond has a first end which is proximate the light source and is optical coupled thereto. The light source and first end of the diamond coupler are in a light reflective chamber. The second end of the diamond coupler extends into a passage way. The diamond coupler's first end extends into the chamber and is proximate the light such that it is light coupled and the second end of the coupler extends into the passage way.

Preferably the diamond is in the form of a rod, and can be synthetic or natural diamond.

A top housing is provided which is formed of a thermally conductive material, such as copper, and can provide cooling of the system. The chamber has reflective surfaces, preferably formed of gold. The reflective surfaces enable efficient transmission into the fiber of light rays traveling at angles greater than 58 degrees from the fiber axis.

The light source is retained within the chamber by a pair of retaining bars. The retaining bars are formed of an electrically conductive material, preferably platinum. Light regulating means can be provide for maintaining the light source at a desired constant emissivity. A diamond plate can be positioned between said diamond coupler and the light source.

The optical fibers have one end extending at least partially into the passage way proximate the diamond coupler and is optically coupled to the diamond coupler. The retaining bars are connected to a power source for powering the light source which can be an infrared radiation generator or can produce narrow band or wide band light.

Preferably, the optical fiber is a chalcogenide glass optical fiber with a plastic coating of from about 10 to about 400 microns thickness, thereby facilitating use in obtaining evanescent-wave absorption spectra of water-containing samples in contact with the coating material. Polytetrafluoroethylene is the preferred coating material.

BRIEF DESCRIPTION OF THE DRAWING

The advantages and objects of the invention will become apparent and the invention will be more fully understood from the following specification, particularly when read in conjunction with the drawings, wherein.

DETAILED DESCRIPTION OF THE INVENTION

Figure 1:
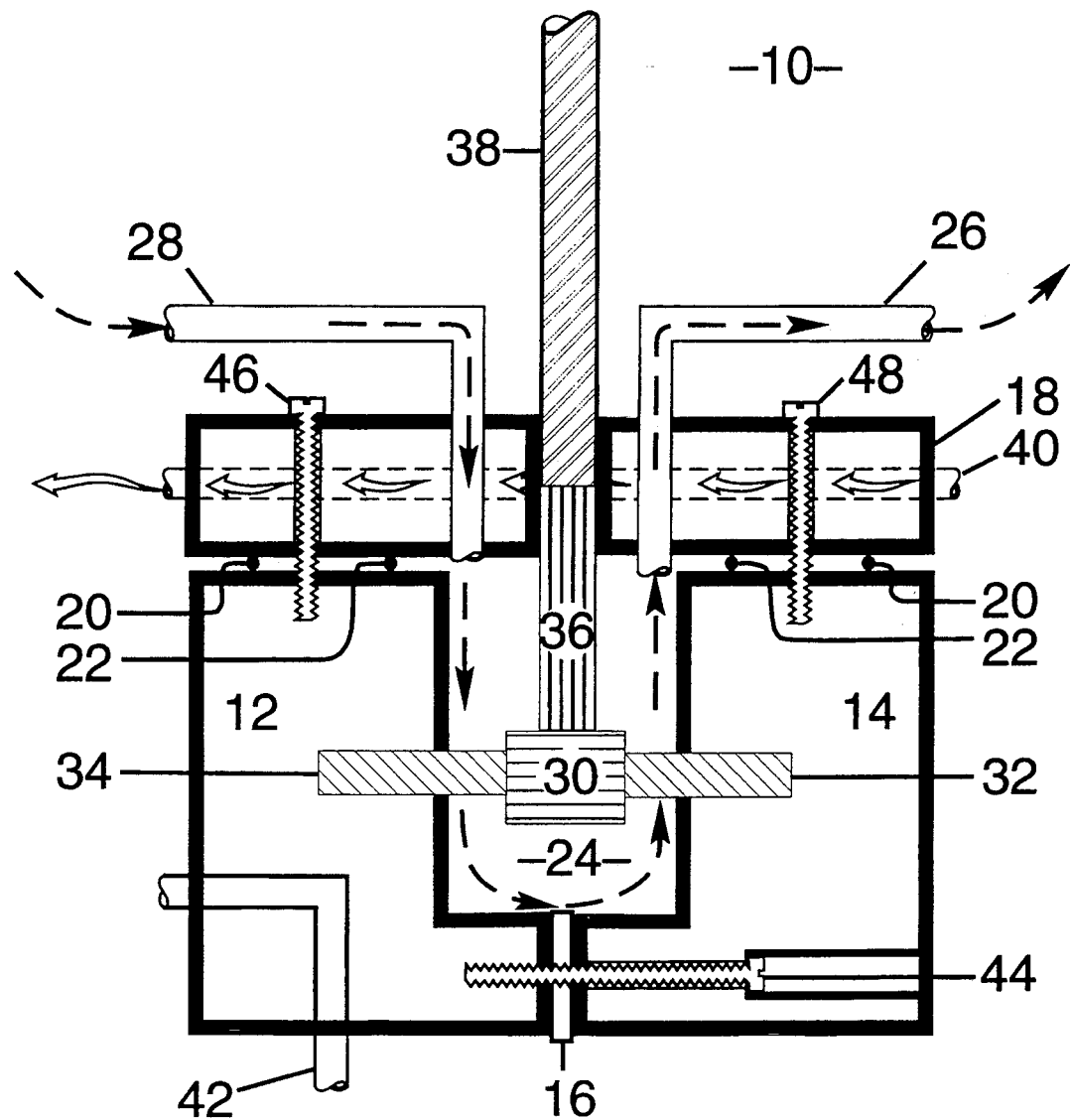
FIG. 1 is a cross-sectional view of the coupling apparatus of the instant invention.

An efficient means of transferring optical radiation from a high-temperature light source into an optical fiber is achieved with direct (lensless) optical coupling through a rod which serves as a light pipe. With this invention, direct-contact optical coupling is obtained between a hot source and an infrared-transmitting optical fiber or fiber bundle, composed of chalcogenide or other material with refractive index of 1.5 or greater, by using a diamond rod as an intermediate medium. This type of coupling is particularly useful when the fiber, in order to retain its useful properties, must be maintained at a lower temperature than the source.

For an on-axis light ray, the reflection loss R at an interface between media with refractive indies $n_1$ and $n_2$ is given by the formula $$R = \frac{(n_1 - n_2)^2}{(n_1 + n_2)^2}$$

For a standard fiber interface through air $n_1 = 1.0$, $n_2 = 2.8$ and $R = 0.22$. This value applies to a typical commercially available chalcogenide fiber. The use of the diamond coupler of the instant disclosure brings this 22% loss down to less than 1%. The $n_1$ for the diamond coupler is 2.4 which is higher than that of air. The SiC source used in the instant invention has a high index of refraction with $n = 2.7$ and reflective loss at its interface with the diamond will also be reduced relative to what it would be with air.

A light ray propagating within a fiber of refractive index $n_1$ will undergo total internal reflection at its interface with a medium of lower refractive index $n_2$, as long as the ray makes an angle 0 with the fiber axis that is less than the complement of the critical angle $\theta_c = \sin^{-1}(n_2/n_1)$. In a chalcogenide fiber where $n_1 = 2.8$, the uncoated fiber when surrounded by air gives a $n_2 = 1$ and $\theta_c = 21°$. For the same fiber in water, $n_2 = 1.33$ and $\theta_c = 28°$. The fiber will therefore transmit a cone of light with a half-angle of 69° in air, and a cone of 62° in water.

Not all of the allowed cone of light can be transmitted into the input end of the fiber using through-air focusing optics. Analysis shows that when the input end of the fiber is cleaved perpendicular to its axis, light that impinges from air onto the fiber at approximately 90° off-axis is refracted to an angle of only 21° off-axis within the fiber. The range of modes transmitted is thus limited in part by the index of refraction of the medium used to transmit light into the fiber.

In the instant disclosure a silicon carbide, SiC, light source is used. It should be noted that other light sources can be substituted. The blackbody radiation which is emitted from the glowing SiC surface into the diamond covers a full $2\pi$ steradians; however, the total internal reflection within the diamond coupler is limited to rays within a cone having a 65° half-angle. Snell's law says that refraction at the diamond-chalcogenide interface will reduce this to $\Phi_w = 51°$ where $\Phi_w$ indicates the half-angle of the cone of light that propagates within the fiber. This definition is also utilized in Katz, M., Bornstein, A., Schnitzer, I., & Katzir, A. (1991) Proc. SPIE 1591, 236-245 wherein $\theta_w$ corresponds with the $\Phi_w$ disclosed herein. This is significantly greater than the value of $\Phi_w = 10°$ expected for light transmitted into the fiber using an $f/1$ lens or mirror. With $\Phi_w = 51°$, all of the light rays will be incident on the lateral surfaces of the fiber at greater than $O_c$ for both air and water and are transmitted via total internal reflection down the entire length of the fiber.

The cone of rays with $\Phi_w = 51°$ largely fills the aperture of the fiber. Calculations show that when the fiber is in water, the diamond coupler allows the input of at least 70%, on a solid angle basis, of the 62° half angle cone of allowed rays. This is because the N.A. of a diamond rod in air is almost as large as that of AsSeTe fiber in water. By comparison, it is difficult to obtain in IR lens or mirror with an N.A. much above 0.5, with the theoretical maximum for such a focusing device operating in air being 1.

FIG. 1 illustrates an apparatus for coupling infrared radiation from a hot source into an optical fiber in accordance with the instant invention. The main housing for the source is made of 3 pieces of gold-coated copper or other electrically-thermally-conductive material with an IR-reflective surface. The main housing for the source and diamond coupler, as illustrated herein, is formed from a 30-mm-dia. copper cylinder which is cut in half forming two side housings 12 and 14. Other materials which provide equal electrical-thermal conductivity can also be used to manufacture the housing and this requirement may vary with the specific design. The housings 12 and 14 are insulated electrically from each other by a 1-mm-thick PTFE gasket 16, or other similar material, to allow them to serve as electrodes. The front of the source chamber is covered by a 6-mm-thick copper top housing 18. The top housing 18 is electrically insulated from the electrodes formed by the two side housings 12 and 14 by small O-rings, or other seals, 20 and larger O-rings, or other seals, 22. Viton O-rings were used herein, however any O-ring or seal providing the same specifications can be used. The seals provided by the gasket 16 and the O-rings 20 and 22 allow the two side housings 12 and 14 and the top housing 18 to contain a small cylindrical chamber 24, approximately 12.5 mm in diameter by 16 mm in length. The top housing 18, as illustrated herein, is equipped with a pair of inlet/outlet ports 26 and 28. The outlet port 26 allows evacuation of the cylindrical chamber 24 and the inlet port 28 allows purging with a slow flow of argon or other inert gas. In the preferred embodiment the chamber 24 is a vacuum, however as this may be difficult to obtain in some instances, a partial vacuum can be used. Alternatively, the top housing 18 and two side housing 12 and 14 can be commercially sealed with a partial or full vacuum within the chamber 24.

The vacuum chamber 24 contains a broadband infrared source element 30, which is a small $2 \times 2.5 \times 3$-mm piece of sintered SiC sectioned from a natural-gas igniter, as commonly used in clothes dryers. In the illustrated embodiment the element 30 has three flat surfaces to allow for optimum contacts. Alternatively, the element 30 can be of any shape as long as it can be secured within the chamber 24 and direct contact made with the diamond coupler 36. Electrical current is carried to and from the source element 30 through platinum rods 32 and 34, approximately 2-mm-dia. $\times$ 10-mm-long platinum rods (Johnson Matthey/AESAR, Seabrook, N.H.). These platinum rods 32 and 34 are press-fit into the inner portion of the two side housings 12 and 14. The platinum rods 32 and 34 support the source element 30 by lateral pressure against 2 of its flat surfaces. Alternatively, electrical current can be supplied to the source 30 through wire or other similar means which can be supported by the rods 32 and 34. If providing the power to the source 30 through alternate means, the rods 32 and 34 can be manufactured from any material which would provide the support and withstand the temperature ranges. Additionally, by providing the power through wire or similar means would exclude the requirement for the two side housings 12 and 14 to be electrically conductive.

A diamond coupler 36, consisting of a 16-sided, 0.5-m-dia., 8.5-mm-long, type IIA ($N_2$ free) natural diamond rod (obtained from Duddledee Harris Diamond Corp. (Arlington, N.J.) is press-fit into a passage 50 in the center of the top housing 18, to a depth which results in the diamond pushing snugly against a flat surface of the source element 30 when the top housing 18 is tightened down against the O-rings 20 and 22. The type IIA diamond provides the qualities which are required, however, other diamond types, or even synthetic diamonds, can be used if they meet the required specifications.

Platinum is the optimum material for the rods 32 and 34 forming the electrical contacts with the heating source 30. Platinum possesses a high melting temperature (2042K), good electrical conductivity, and a low reactivity towards silicon carbide, even at the high working temperature of the infrared source 30.

An inexpensive thin flat diamond plate, a 0.050-mm-thick, ~2-mm dia. type IA diamond plate (not shown), may intervene between the diamond coupler 36 and the source element 30, in order to protect the diamond coupler 36 from thermal damage or chemical attack caused by brief accidental overheating of the source element 30.

The radiation emitted from the hot flat surface of the source element 30 passes into the flat, polished end of the diamond coupler 36, which touches or is close to the hot emissive surface of the source element 30. The separation must be less than the shortest wavelength of light to being transmitted into the fiber, to allow the radiation to enter the diamond coupler 36 while experiencing very little reflective loss. This is due to the close match in the indices of refraction of silicon carbide and diamond, which are both substantially higher than that of air. A separation greater than the wave length being transmitted allows for a reflective loss of about 20%.

The light-input end of the optical fiber 38 abuts the output end of the diamond coupler 36 inside the center of the 0.5-mm passage 50 in the top housing 18. Within the top housing 18 are one or more parallel channels 40 which run close to the junction of the diamond coupler 36 and the optical fiber 38. Tube fittings on the ends of these channels allow water flow to keep the optical fiber 38 cool when the infrared source 30 is hot. Inside the two side housings 12 and 14 additional channels 42 can be provided to allow the passage of cooling air. The two side housings 12 and 14 are held together by screws and the top housing 18 is attached to the two side housings 12 and 14 through screws 46 and 48. The screws 44, 46 and 48 are equipped with nylon screw insulators to prevent them from short-circuiting the electrodes. As previously stated, the top housing 18 and the two side housing 12 and 14 can be commercially sealed, eliminating the requirement for screws or other securing methods.

The infrared source 30 is heated electrically using a low-voltage (5–10 V), high-current (5-A) power supply, to a temperature of 1100–1800K. Alternatively, a high temperature of the photoemissive material could be produced by any of a number of other means besides electrical heating, e.g. illumination with a laser. A feedback regulator of the source temperature can be added if desired.

The complete or partial vacuum in the chamber 24 surrounding the heating source 30 helps to reduce the power dissipated by conduction and convection from the source to the two side housings 12 and 14. Radiative transfer of heat is reduced by coating the inside surface of these other elements with an IR-reflective material, gold being the preferred embodiment coating.

Diamonds form thin films of carbon on its surface at temperatures above ~900° K. in air, but in the absence of oxygen is stable up to ~1800° K. For this reason, when the heating source 30 is operated at temperatures above ~900° K. the air in the vacuum chamber 24 is replaced with a low pressure of argon or other inert gas. The diamond coupler 36 is cylindrical with a cross-section which is similar to that of the fiber or fiber bundle. To avoid risking damage to the diamond coupler, operation should be well under the ~1800° K. temperature limit.

In the preferred embodiment, the diamond is cut from a naturally-occurring Type IIA gemstone, or synthetic equivalent, into a cylinder whose cross-section is a regular 16-gon of diameter ~0.5 mm and length ~8.5 mm. As stated, other types of natural or synthetic diamonds can be used, with resultant change in spectral transmission range. Having a high refractive index and low absorbance at most optical wavelengths, the diamond coupler 36 serves as a low-loss light pipe for the broadband light from the source 30. Most of the light rays that impinge on the lateral surfaces of the diamond coupler will undergo total internal reflection and be propagated along the length of the coupler. A Type IIA diamond has properties which make it uniquely well-suited for this application, including its wide spectral transmission range, its high refractive index, and especially its extremely low thermal expansion coefficient ($1.5-4.8 \times 10^{-6}$ at temperatures up to 1200°K.), which allows it to withstand a thermal gradient of 1000–1500° K.-cm$^{-1}$ without cracking.

Figure 2:
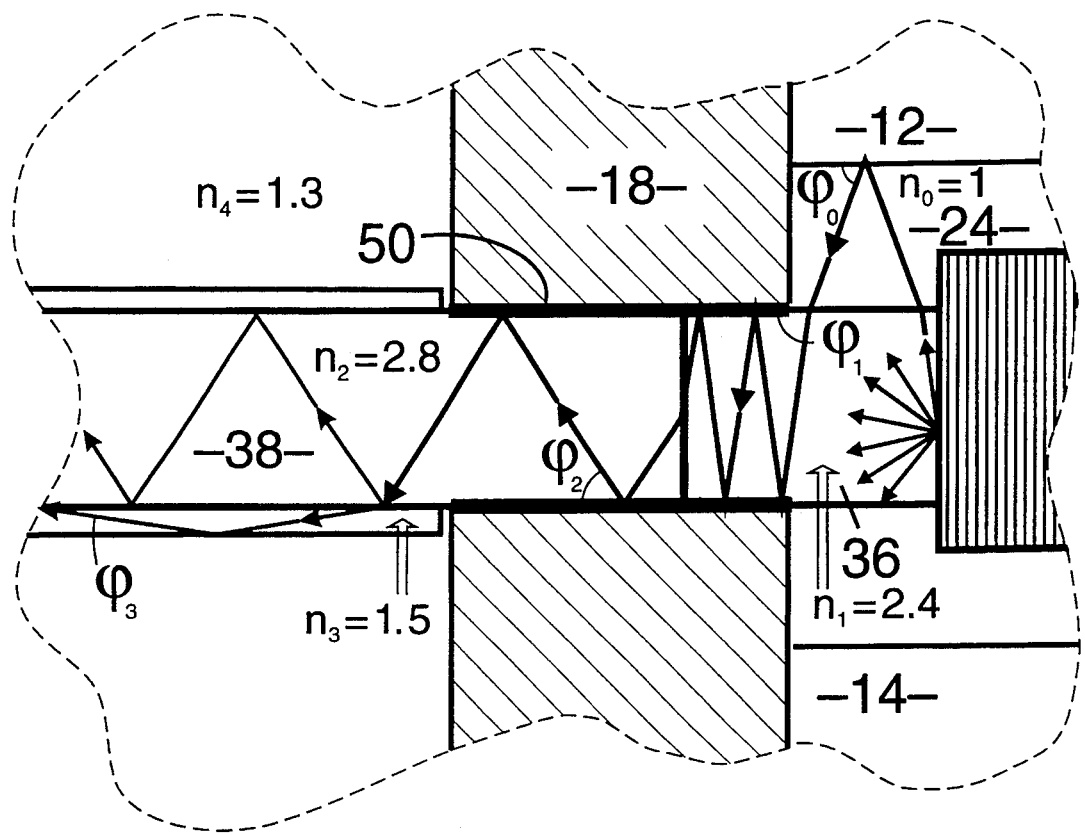
FIG. 2 is a cross-sectional view of a portion of the apparatus of FIG. 1 tracing the path of a meridional ray.

As shown in FIG. 2 a propagation angle of nearly 90° off-axis is needed for a ray to propagate within the fiber at an angle of $\phi_2 = 58°$. In fact, the meridional rays which end up propagating within the fiber at $\phi_2$ angles between 58° and 59° start out within the space surrounding the sides of the diamond coupler 36 at $\phi$ angles between 65.6° and 90° off axis. These high order rays will pass into the portion of the cylindrical vacuum chamber 24 surrounding the diamond coupler 36. The high-order rays are reflected by the gold coating on the cylindrical vacuum chamber 24 back towards the diamond coupler 36. The high-order light rays are then reflected back into the diamond coupler 36 until they pass into the portion of the diamond coupler 36 within the top housing 18. The range of rays that can undergo reflection at these angles represents a relatively large range within the chamber 24 and corresponds to a solid angle of $0.8\pi$, all of which are collected by the diamond and compressed into a very narrow angular range. Once the rays pass into this region, all rays are reflected from the diamond coupler's 36 lateral surfaces which are in contact with the highly-reflective gold-coated surfaces of the top housing 18. Due to the reflective qualities of the gold, all rays propagate forward through the diamond coupler 36 with low losses, until they reach the optical fiber 38.

The end of the diamond coupler 36 that is in contact with the fiber 38 is a flat polished face to be in immediate contact with the end of the optical fiber 38. The optical fiber 38 is, according to prior art, manufactured of chalcogenide glass or other IR-transparent material with an equally flat surface. The surfaces do not have to be vertical, however they must be smooth, matching surfaces to allow for maximum transference of the rays. If angled, the rays will bend, however this bend is minimal and may be useful in some instances. The use of an optical fiber 38 material with an index of refraction similar to that of the diamond coupler 36 insures that the losses due to reflection at the coupler 36 or coupler 36 to fiber 38 interface are minimal. As a result of this, the infrared light intensity entering the fiber 38 and propagating down its length will again be nearly as great as at the emissive surface of the hot source element 30. It should be noted that while this is true of electromagnetic radiation at optical wavelengths, it is not true of thermal radiation at very long wavelengths, such as the far infrared or microwave regions which would be absorbed by the optical fiber and thus cause a rise in its temperature. This potentially damaging thermal radiation is not radiatively propagated to the fiber but is instead absorbed by the cooled gold-coated top housing 18 which is in contact with the junction between the diamond coupler 36 and optical fiber 38.

In addition to decreasing reflection losses, the close match of indices of refraction greatly increases the range of angles that can be propagated through the optical fiber 38. With the diamond coupler 36 and a chalcogenide fiber of refractive index 2.8, the allowed angles range from nearly on-axis to about 61° off-axis. The latter angle is very near to the maximum angle which can be propagated down the optical fiber 38 via internal reflection. The instant device allows for ~66% of the possible subcritical rays to be transmitted into the optical fiber 38 through the diamond coupler 36, whereas using the same fiber with a focusing optic in air only ~11% are transmitted. The additional light rays represent a ~6-fold increase in the energy throughput of the system. Another way of saying this is that the numerical aperture is increased by a factor of at least the square-root of 6 relative to that achievable with focusing optics operating in air.

One of the advantages of this wide numerical aperture is that high-order modes are easily transmitted into the fiber. In general, for maximum spectral sensitivity it is desirable to make use of the highest-order modes that can be propagated within the fiber. This is because the measured evanescent-wave absorbance is proportional to the product of 3 factors: (1) the penetration depth, (2) the interfacial evanescent intensity; and (3) the number of reflections per unit length. All three of these factors are larger for higher-order modes.

For a fiber with a coating or cladding thicker than the penetration depth, an evanescent wave does not penetrate significantly into the coating and it will not be possible to detect absorbance from materials in contact with the coating. However, if sufficiently high-order optical modes are excited within the fiber, then the optical field within the coating is no longer evanescent. In this case the ray can leave the fiber and propagate all the way through the coating layer, although refraction will cause this light ray to become more parallel to the fiber axis, as illustrated in FIG. 2. Whether such a ray will exit from the coating layer or will be reflected back from its external surface then depends on the relative indices of refraction of the coating and the external medium. If the coating has an index of refraction ($n_3$) intermediate between that of the fiber ($n_2$) and the external medium ($n_4$), then there will be a range of light rays that are not totally reflected at the fiber-coating interface, but are totally reflected at the coating-sample interface. (Harrick, N.J. (1967) Internal Reflection Spectroscopy (Interscience Publishers—John Wiley and Sons, New York) and (Reichert, W. M. (1989) Critical Reviews in Biocompatibility 5, 173.)

Using an approximate value of $n_3 = 1.5$, light rays propagating within the fiber itself at angles between $\phi_2 = 57.6°$ and $\phi_2 = 61.6°$ can propagate outward through coating, yet still be totally reflected at the coating/water interface. As long as the coating's surface is parallel to that of the fiber, $d_p$ for these modes into the surrounding aqueous sample is the same as if the fiber were uncoated. Furthermore, the interfacial evanescent intensity, although it is expected to exhibit a periodic oscillatory dependence on the normalized thickness (coating thickness divide by wavelength), is approximately the same as if no coating were present.

Thus, the presence of an IR-transparent plastic coating on a fiber is not necessarily expected to lead to a decrease in measured evanescent wave absorbances. Instead, the coating can actually lead to a significant increase in measured absorbance, as has been shown previously for optical cavities coupled to other types of internal reflection elements (IREs). (See Harrick et al).

These effects can only be observed if rays with sufficiently large value of $\phi_2$ are present within the fiber, since evanescent-waves of rays that are nearly on-axis will only slightly penetrate into the plastic coating but will not reach its external surface in contact with the sample. As stated, the cone of rays that propagates via total internal reflectance within the diamond coupler is reduced to a cone with half-angle $\Phi_w = 51°$ within the AsSeTe fiber. Thus, it would be expected that none of the rays propagating through the diamond coupler could continue into the fiber at a sufficiently high angle to propagate through the plastic coating. However, with the instant invention, high-angle rays that leave the diamond are reflected off the gold-coated walls of the housings 18, 12 and 14 a way that allows them eventually to reach the fiber 38. The gold-coated cylindrical surfaces of the housings 18, 12 and 14 thus act as a light pipe, enabling very-high-order modes to be excited within the fiber.

It should be noted that a subset of these high-order modes can also be transmitted into the fiber using traditional through-air focusing optics, but in order to do so it is necessary to cleave or mold end of the fiber at an oblique angle.

The infrared reflective passage 50 through the top housing 18 is machined, with a close tolerance, to the same diameter as the diamond coupler 36 and optical fiber 38, allowing for optimum heat transfer and optimal stability of the diamond 36 source 30 contact. The passage 50 also results in a built-in precise axial alignment of the infrared source 30 and optical fiber 38. This eliminates tedious optical alignment procedures for the input end of the fiber that are required with through-air focusing optics. Furthermore, no antireflection coating on the input end of the fiber is needed to keep reflection losses below 1%, because the indices of refraction of the SiC source 30, the diamond coupler 36, and the AsSeTe fiber 38 are well-matched. The diamond coupler 36, while more expensive than an antireflection coating on a single fiber, will in the long term be economical because the relatively fragile fibers used for infrared evanescent-wave spectroscopy require periodic replacement.

With the instant invention, light passing through the optical fiber 38 can be used for evanescent-wave absorption spectroscopic analysis of materials either contacting its surface directly or contacting a low-refractive-index coating on the curved lateral surface of the fiber. The latter arrangement is possible only because the diamond coupler 36 transmits into the optical fiber 38 a very wide range of modes, some of which are capable of being guided through the fiber's 38 transparent plastic coating and used for evanescent wave spectroscopy at its external surface.

In the preferred embodiment, a polyamide-coated chalcogenide fiber is used. Henkel Macromelt (R) 6071 polyamide was used, however a polyamide or poly (tetrafluoroethylene) having similar optical properties can also be used. Plastic coated AsSeTe optical fibers from Amorphous Materials, Inc. were selected, in part, due to their greater flexibility of the fiber material relative other commercially-available chalcogenides. (Hilton S., A. R. (1991) Proc. SPIE 1591, 34–42). Fibers are heated at ~363° K. within a small-dia. glass tube. This heating procedure helps to straighten the fiber. If plastic-coated fiber is to be used, the fiber is soaked in $CH_2Cl_2$ for 3–5 h while being held vertically in a 3-mm-dia. glass tube. This thins the coating somewhat and helps to make it more uniform.

A fresh razor blade is used to cleave coated or uncoated fiber to a length of 47 cm. One end is cleaved perpendicular to the fiber axis, while the other is cleaved at an angle of 40±5° away from perpendicular.

To use the diamond optical coupler for the evanescent-wave absorption study of bulk materials, the perpendicular-cleaved end of the fiber 38 is inserted into the 0.5-mm passage 50 in the cooled top housing 18 until it is in direct contact with the diamond coupler 36. The fiber is supported in two fiber chucks, with its central portion of the fiber passing through a 12.5-cm-deep × 15-cm-wide liquid through made of PTFE. The holes through which the fiber passes at the 2 ends of this trough are vertically offset to produce a 10° tilt of the fiber away from horizontal. This tilt allows varying the interaction length of the fiber with a liquid in the trough simply by raising or lowering the level of the sample.

Additionally, a poly-(tetrafluoroethylene) coating has similar properties, insofar as this invention is concerned, and can be substituted. These coatings protect the fiber from mechanical stresses and chemical damage by air and/or water, and also protect the sample from contact with a surface-active and potentially toxic optical fiber material.

Light is collected from the angle-cleaved output end of the fiber and collimated by means of a simplified version of standard Cassegrain optics. The fiber lies along the axis of a gold-coated 75-mm-dia., 37-mm focal length on-axis paraboloid mirror (Janos Technology, Inc., Townsend, Vt.), which was special-ordered with a 1-mm-dia. hole to allow the passage of the optical fiber through its midpoint. This mirror fits neatly in the external source port hole of the Nicolet 60SXR spectrometer, permitting the use of a standard port cover plate as a mirror mount. (Note, however, that the standard port hole requires a slight enlargement with a file in order to accommodate the 3-in.-dia. mirror). To enter the spectrometer, then, the fiber passes through 1-mm-dia. holes in the port cover plate and the mirror (which has its reflective surface facing the interior of the spectrometer). To keep the flexible fiber from bowing away from the optical axis, it is supported by a 40-mm long, 1-mm-dia. glass capillary which just fits in the mirror's hole. Inside the spectrometer, the output end of the fiber points toward and is situated ~2–3 mm from a flat 3×3 mm first-surface mirror (Edmund Scientific, Barrington, N.J.). This small mirror is mounted on a narrow horizontal finger, with its front surface located just a few mm inside the focal point of the paraboloid. The small flat mirror reflects the output from the optical fiber backwards towards the paraboloid mirror, which culminates the light and re-directs it forward along the normal emission beam path of the Nicolet 60SXR spectrometer. With this Cassegrain collimator, a portion of the light (including that which is on-axis) is blocked by both the fiber itself and the finger on which the small mirror is mounted, but this occlusion largely overlaps that due to the HeNe reference laser detector and mount of the Nicolet 60SXR interferometer. To optimize this collimator for a fiber cleaved at ~40° off-perpendicular, the small flat mirror must be tilted at ~20° and the fiber end must be shifted slightly (~2 mm) away from the optical axis. FIGS. 3–15 illustrate the results of measurements taken with both uncoated and plastic-coated chalcogenide fibers. A Nicolet 60SXR spectrometer equipped with a liquid-nitrogen-cooled MCT-A detector with a $(0.25\ mm)^2$ element (Belov Technology Co., Inc., New Brunswick, N.J.) was mounted on the standard detector port of the spectrometer. Use of the small detector size reduces noise in the spectra, since it allows filling more of the detector area with the image of the output end of the 0.5-mm-dia. fiber.

All data in this disclosure was obtained with 4-$cm^{-1}$ spectral resolution, retardation velocity of 100 cm/s, and an electronic gain setting of 16, and are plotted without any smoothing.

The small flat mirror reflects the output from the optical fiber backwards towards the paraboloid mirror, which culminates the light and re-directs it forward along the normal emission beam path of the Nicolet 60SXR spectrometer. With this f/0.5 collimator, only a subset of the wide cone of rays propagating through the fiber can actually be brought to focus on the infrared detector. However, different subsets can be selected quite easily, simply by cleaving the output end of the fiber at different angles. The more oblique the cleavage angle, the more light will be collected from high-order modes. To optimize the collimator for a fiber cleaved away from perpendicular, the small flat mirror must be tilted and the fiber end must be shifted away from the optical axis.

Figure 3:
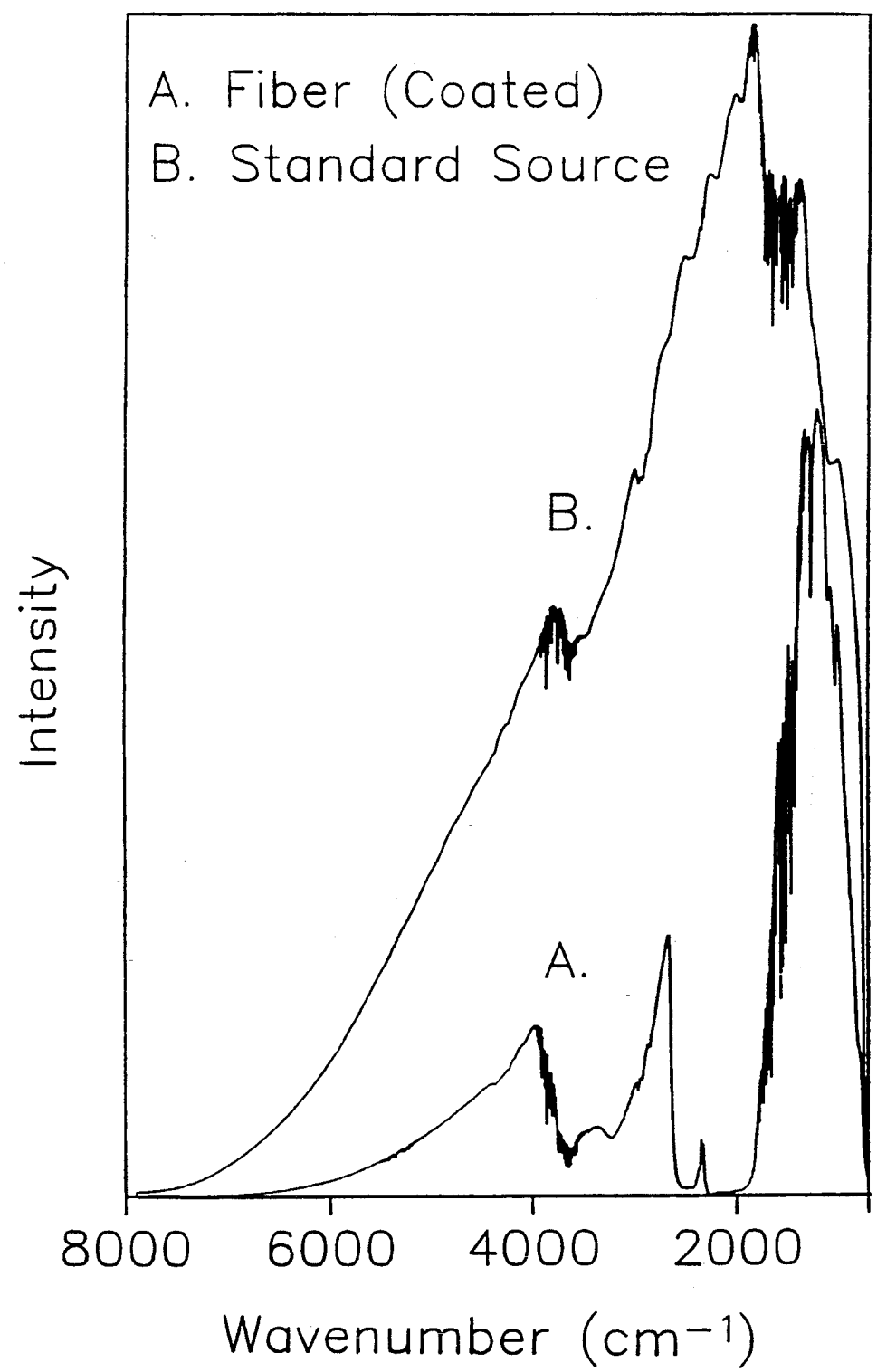
FIG. 3 is a spectrum graph comparing energy throughput of the instant invention and a standard energy source in the empty spectrometer.

FIG. 3 illustrates the single-beam energy spectrum of the light emanating from the end of a 47-cm length of 0.5-mm-dia. polyamide-coated AsSeTe optical fiber using the diamond coupler and broadband IR source of the instant invention. The plastic coating on the fiber used for FIG. 3 was approximately 0.1 mm in thickness. Spectrum (A) is directly compared to (B), in which the uncorrected energy spectrum of the light from the standard infrared source of this spectrometer, known as a Glowbar(TM) is presented. The redder operating color of the SiC indicated operation at a lower temperature than the standard orange-colored Glowbar(TM) (at ~1500K). This was confirmed by comparisons of the throughput spectra to theoretical blackbody curves. This indicated the SiC source was operating at about ~1200° K. This can be brought up to ~1500° K. without risking damage to the diamond and would more than double the energy transmitted into the fiber. For spectrum (B), the standard (f/4) culminating optics within the spectrometer were used, and the beam iris was set at its minimum diameter to 0.68 mm. All other spectrometer settings (resolution, measurement time, etc.) were identical with those used to obtain spectrum (A). The output from this iris was collimated into the interferometer using the spectrometer's standard mirror ($f=37$ mm mirror used to collect light from the fiber). This means that the image size of the 690-$\mu$m aperture on the detector should be quite similar to the image size of the fiber's end. Thus, the ~75% throughput decrease in the 1000–1400 cm$^{-1}$ region for the fiber apparatus relative to an open beam is not due to the narrowness of the fiber. Instead, the principal reason is probably the lower source temperature; additional loss factors are reflection loss at the output end of the fiber, and imperfect optical contact between the diamond coupler 36 and the source 38. As can be seen from these results, the light energy transmitted through the narrow fiber is a large fraction of that transmitted through the empty spectrometer. Furthermore, the throughput is higher, by at least a factor of 4, than is obtainable using the same optical fiber in combination with the prior art, such as a high-aperture off-axis paraboloid mirror, to focus light from the standard source onto the end of the fiber.

Figure 5:
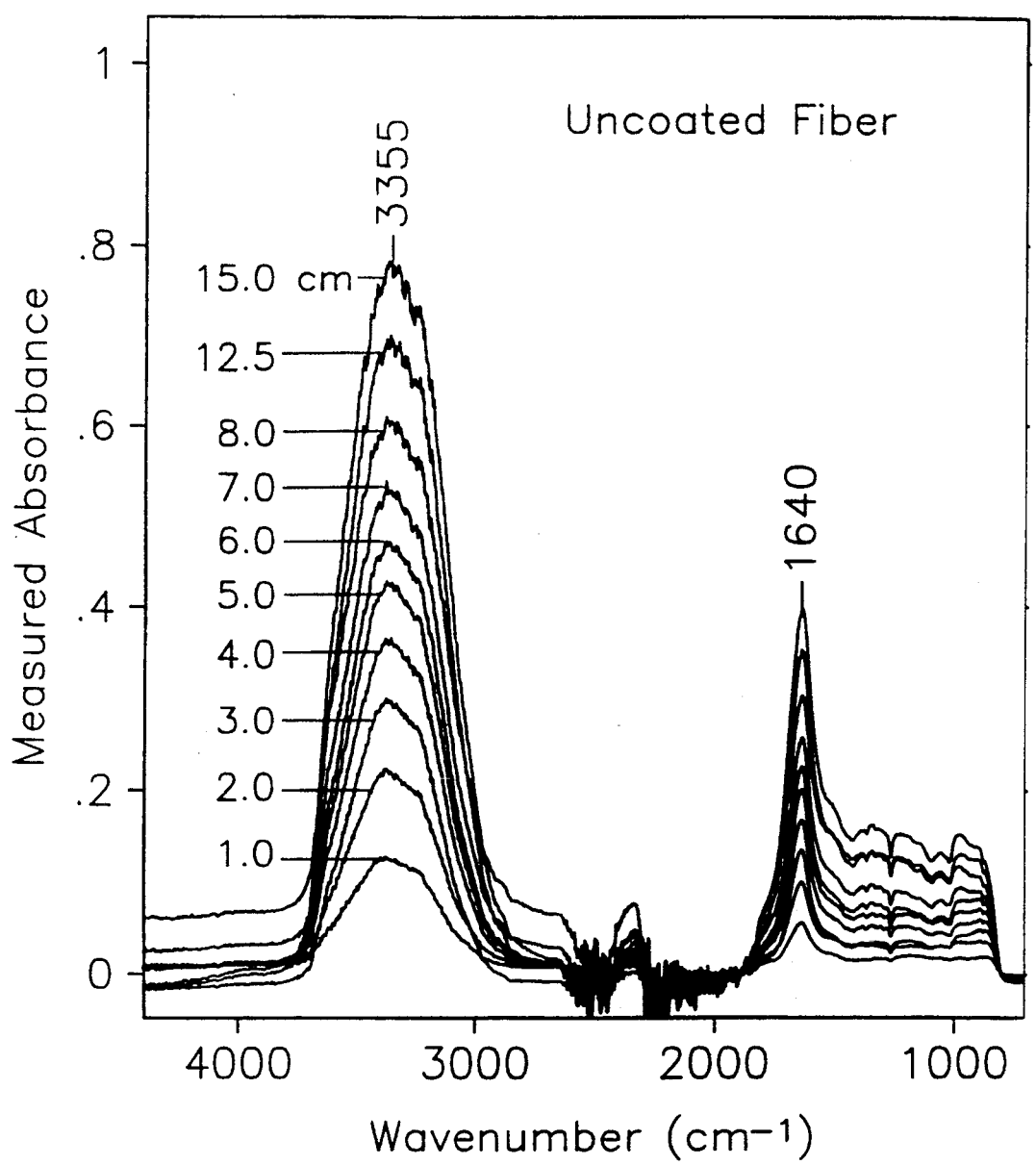
FIG. 5 is a graph illustrating $H_2O$ absorbance for uncoated fibers using the instant invention.
Figure 6:
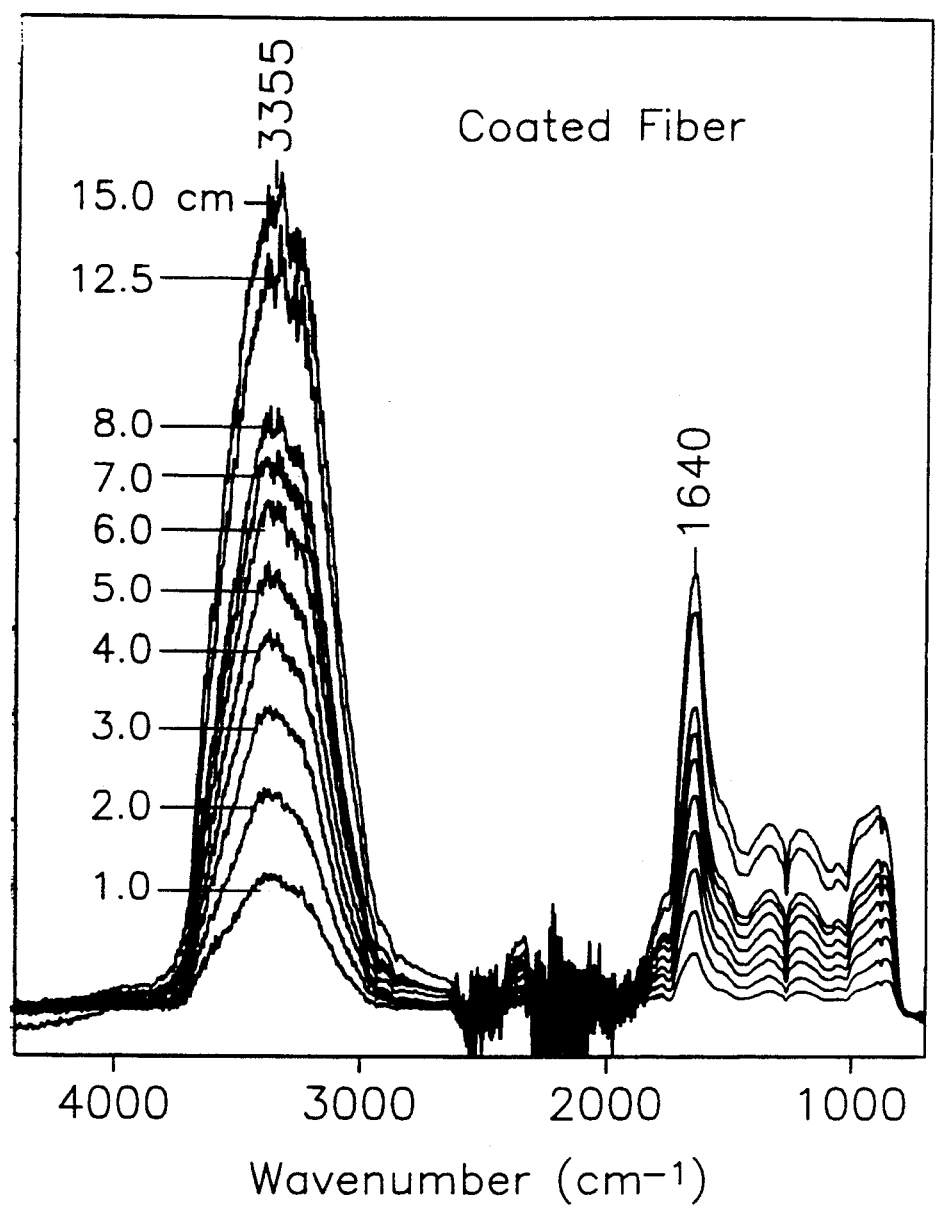
FIG. 6 is a graph illustrating $H_2O$ absorbance for coated fibers using the instant invention.

Further decreases in fiber throughput as other spectral regions are due to material absorbances. For example, the cutoffs at high and low frequency are predominantly due to absorbance by the AsSeTe fiber itself (Hilton, S., A. R. (1991) Proc. SPIE 1591, 34–42). Absorbance due to the 8.5-mm-long diamond coupler is observable particularly between ~1900–2200 and ~2900–3700 cm$^{-1}$. Type IIA diamond absorbs up to ~70% of the transmitted light per mm of path length in the range ~1900–2200 cm$^{-1}$ and up to ~35% per mm in the range ~2900–3700 cm$^{-1}$ (Seal, M. & van Enckevort, M. J. P. (1988) Proc. SPIE 969, 144). Thus, to increase throughput in these spectral regions, it would be necessary to use a shorter diamond coupler. The amount of length reduction is determined by the maximum thermal gradient that can be sustained within the coupler and housing, as well as by the mechanical stability of the press-fitted coupler in the copper end plate. FIGS. 5 and 6 respectively show absorbance spectra of water taken with the preferred embodiment of the optical coupler. The indicated lengths of the fiber were submerged and an uncoated, FIG. 5, and plastic-coated fiber, FIG. 6, was used. The intense features at ~3355 and 1640 cm$^{-1}$, as well as the broad background absorbance in the ~900–1500 cm$^{-1}$ region, are all readily identifiable as water absorptions.

Figure 4:
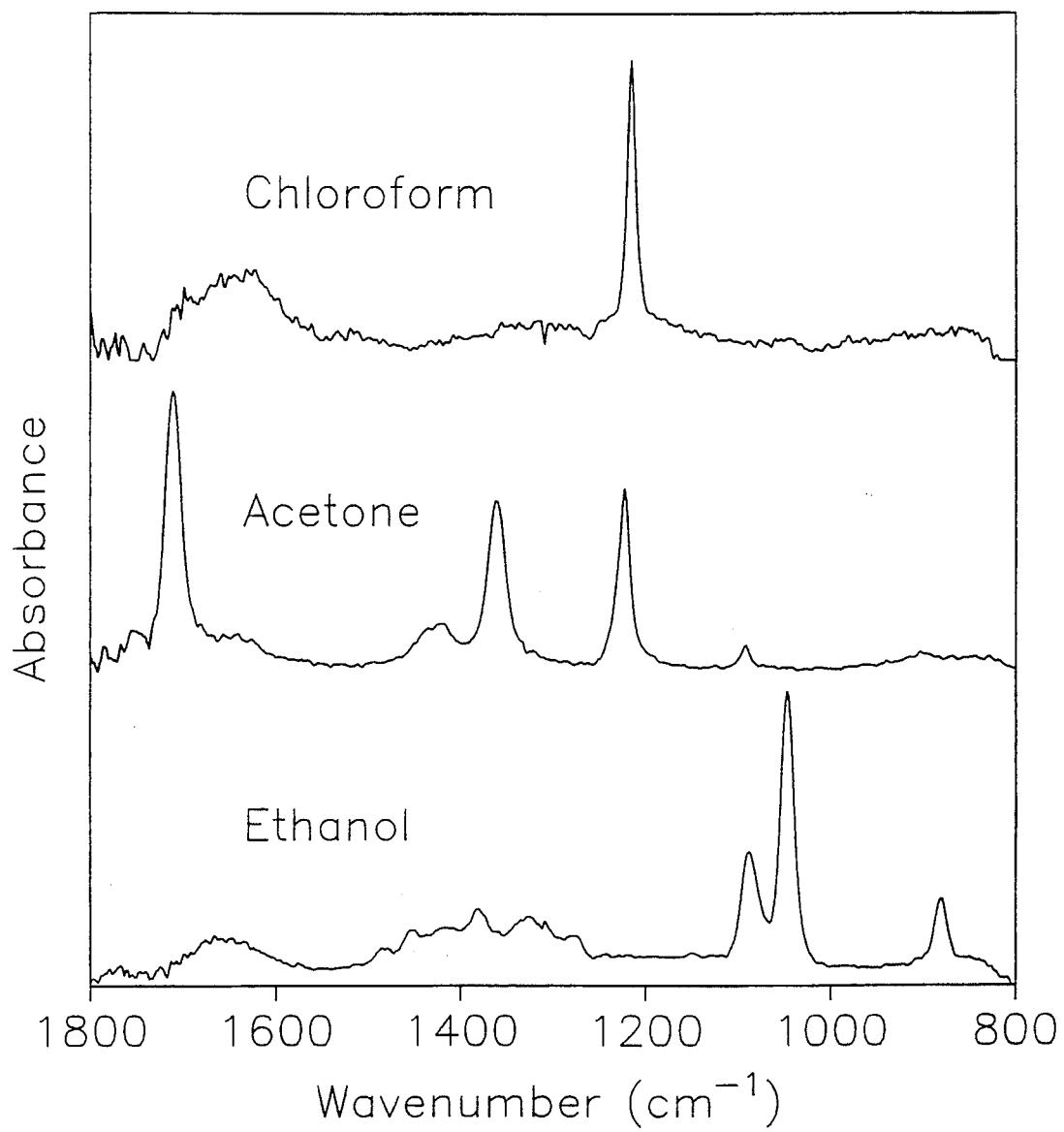
FIG. 4 is a graph identifying three organic solvents with the instant invention.

Spectra of 2–4 $\mu$l samples of 3 different non organic solvents, chloroform, acetone and ethanol, obtained using the instant invention are shown in FIG. 4. Each spectrum was obtained in 22 s (not including an equal amount of time used to scan the background spectrum of the dry fiber). The chloroform, acetone, and ethanol samples were simply dripped onto the uncoated fiber from a syringe, and were spread (using the syringe needle) over a 1 cm fiber segment continuously during the scan periods. By the end of the scans, the samples had nearly evaporated. These spectra demonstrate the convenience, speed, and sensitivity of the instant invention for obtaining spectra of microvolumes of pure liquids.

Figure 15:
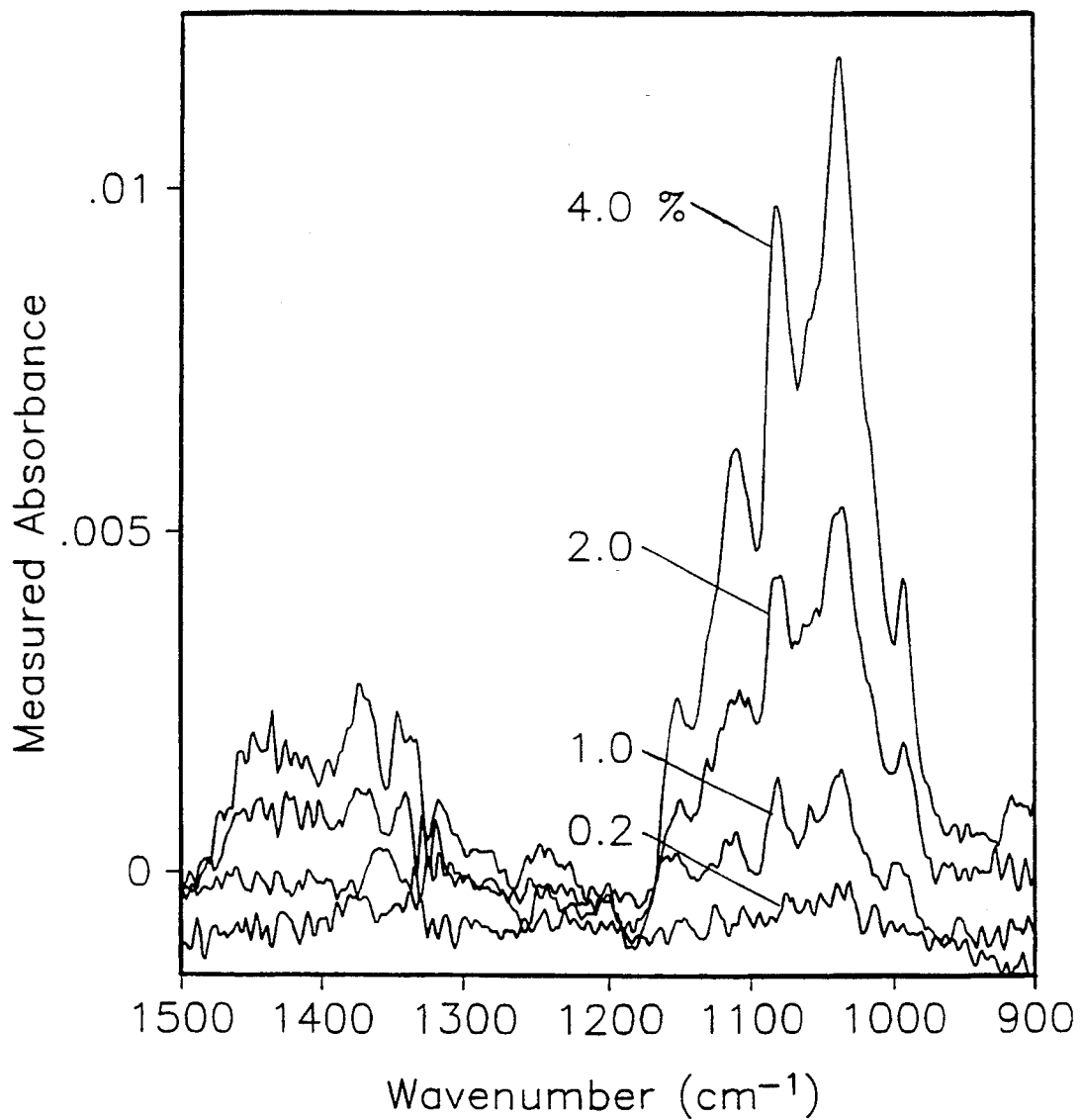
FIG. 15 is a graph illustrating the infrared absorbance of glucose in water using the instant invention.

FIG. 15 shows the absorption spectra of glucose in water at the indicated weight concentrations, using a polyamide-coated chalcogenide fiber and a 2.5-cm submersion length. Each spectrum was obtained with a 70 s measurement time, using a reference scan measured for the same amount of time using pure water. In this figure, each spectral baseline was adjusted by subtraction of a quadratic function covering the range 1500–900 cm$^{-1}$.

Evanescent-wave spectra have previously been obtained using plastic-coated fibers only when sample molecules diffuse into the coating material (Heo, J., Rodrigues, M., Saggese, S. J. and Sigel, J., G. H. (1991) Applied Optics 30, 3944–3951; Ruddy, V., McCabe, S., and MacCraith, B. D. (1990) Appl. Spectros. 44, 1461–1463; Ruddy, V. (1991) Proc. SPIE 1591, 180–187. The evanescent-wave absorption is not due to diffusion of water into the plastic, because water bands appeared in the single-beam spectrum without any measurable delay (<1 s) after dipping the fiber into the solution. Upon removing the fiber and wiping it off, the spectrum equally quickly returned to its original (unsubmerged) appearance and remained constant thereafter. If water were diffusing through a porous coating, the spectral absorbances to rise and fall more slowly after such changes. The measured absorbances are also not due to a rapid leakage of bulk solution through breaks in the plastic coating, since the latter appeared smooth and unbroken under a 10x microscope with a fairly uniform thickness of ~100 $\mu$m.

The evanescent-wave absorption spectrum through the plastic is due to the diamond coupler being capable of collecting light from a fairly large solid angle and refracting it in such a way that it is transmitted into the fiber in a relatively narrow range of high-order modes that can penetrate the fiber-coating interface while still being totally reflected at the coating-water innerface. These modes are giving rise to the evanescent-wave absorption spectra with the plastic-coated fibers.

Figure 7:
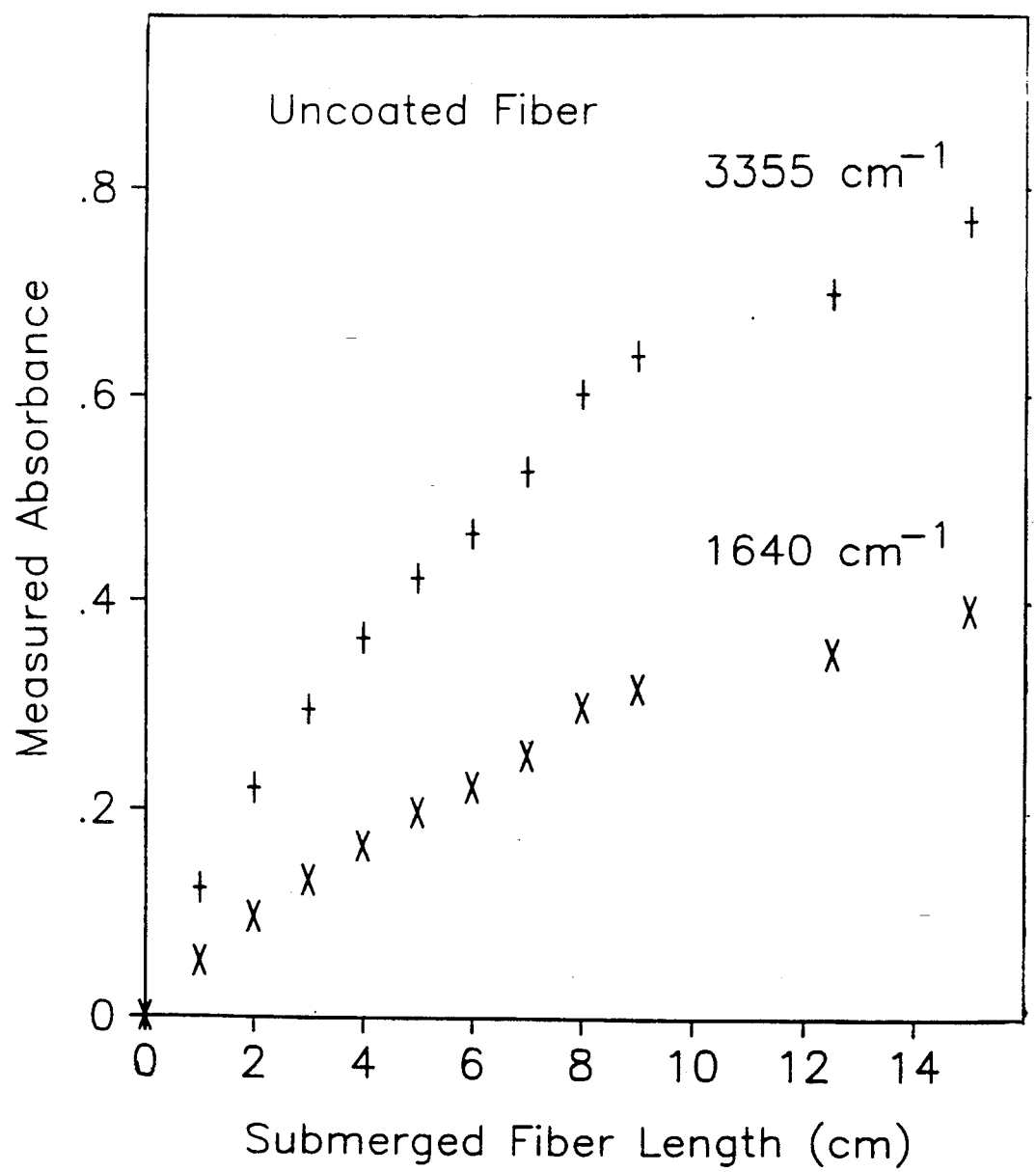
FIG. 7 is a graph illustrating the maximum measured $H_2O$ absorbance for uncoated fibers at two identified wave numbers using the instant invention.
Figure 8:
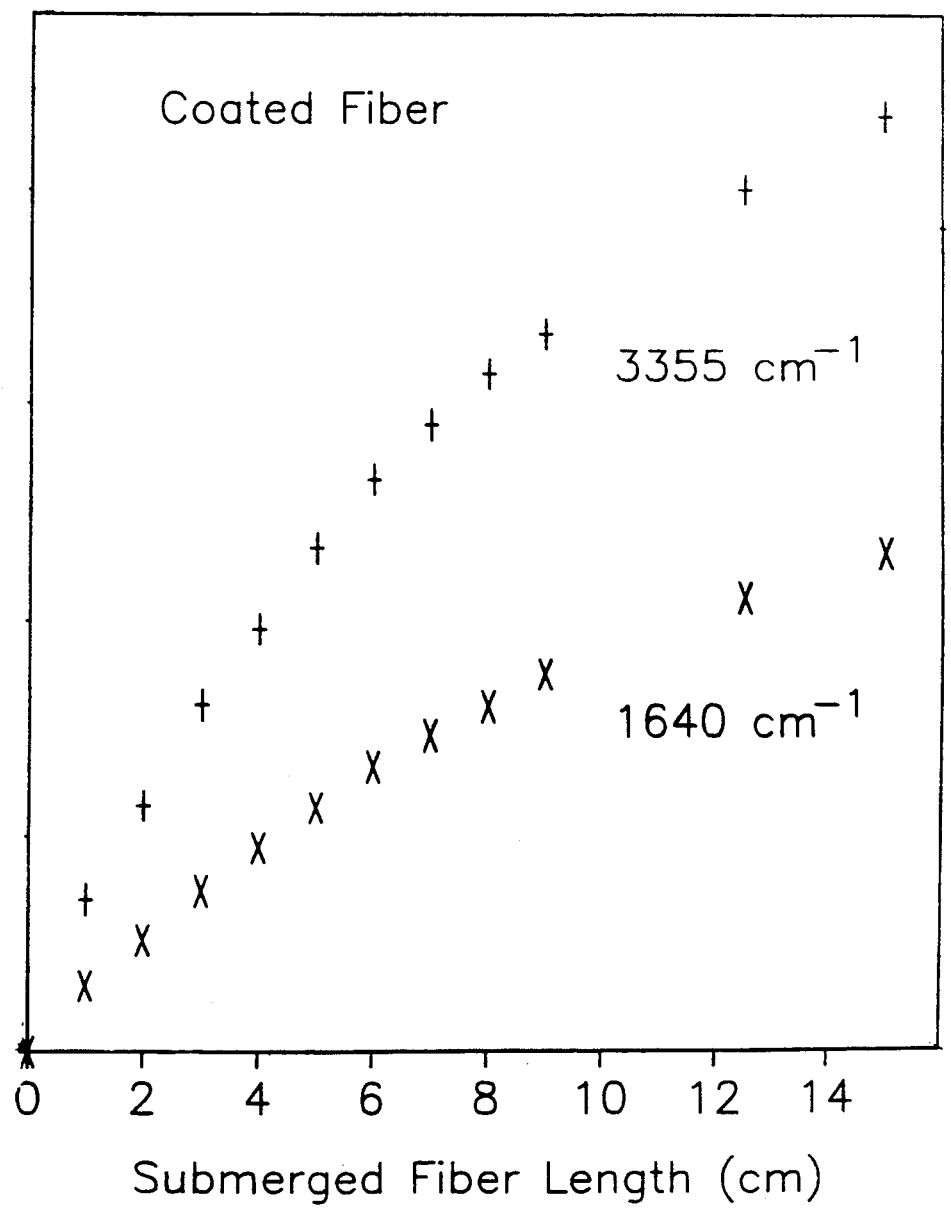
FIG. 8 is a graph illustrating the maximum measured $H_2O$ absorbance for coated fibers at two identified wave numbers using the instant invention.

FIGS. 7 and 8 show plots of the water absorbances at 3355 and 1640 cm$^{-1}$ vs. fiber submersion length for uncoated FIG. 7 and coated fiber FIG. 8. These plots are made from the spectra shown in FIGS. 5 and 6. The peaks both show nonlinearities for submersion lengths above ~8 cm. As reported in Simhony, S., Schnitzer, I., Katzir, A. and Kosower, E. M. (1988) J. Appl. Phys. 64, 3732–3734, this is due to the mix of effective total path lengths for different optical modes present in the fiber.

The absorbance values measured with the plastic coating in place are actually higher than those measured with similar lengths of the uncoated fiber, and at least as linear. The plastic coating behaves as a thin-film waveguide, capable of carrying a significant fraction of the power transmitted down the fiber with a large number of reflections per unit length. The fact that the plastic-coated fiber has an approximately-linear response up to an absorbance value of at least ~0.85 (FIG. 8) indicates that most of the measuring light at ~3400 cm$^{-1}$ must be carried through the plastic coating, where it can be absorbed by the surrounding water.

Figure 9:
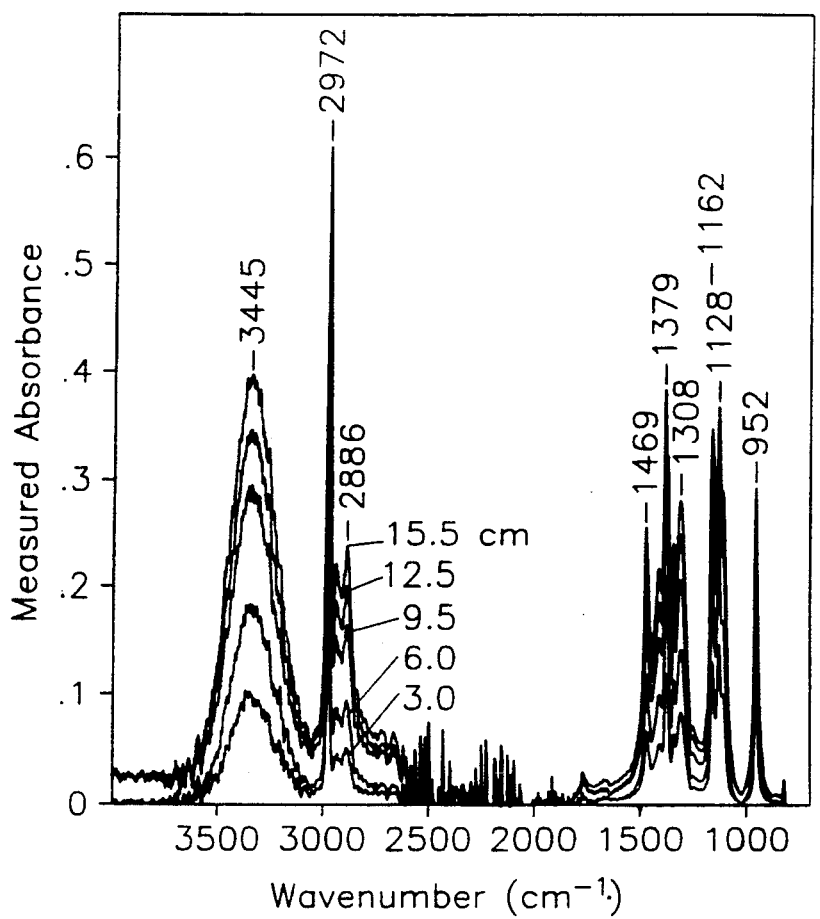
FIG. 9 is a graph illustrating isopropanol absorbance using uncoated fibers at 256 spectral scans with the instant invention.
Figure 10:
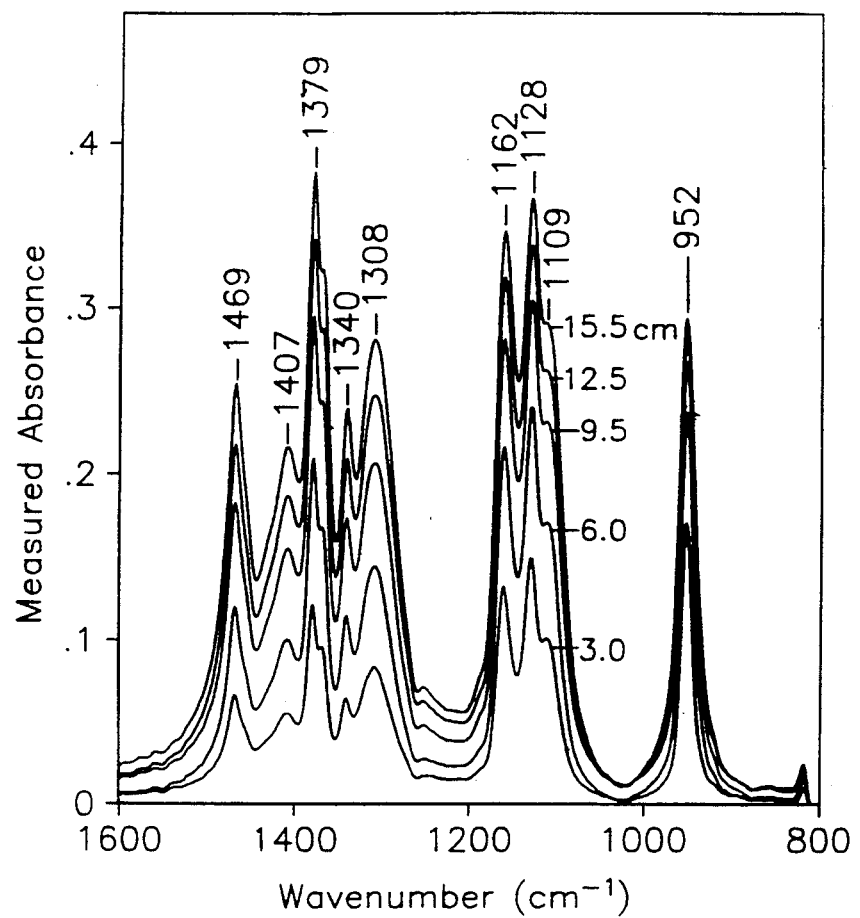
FIG. 10 is a graph illustrating isopropanol absorbance using uncoated fibers of FIG. 9 at 1600–800 $cm^{-1}$ with the instant invention.
Figure 11:
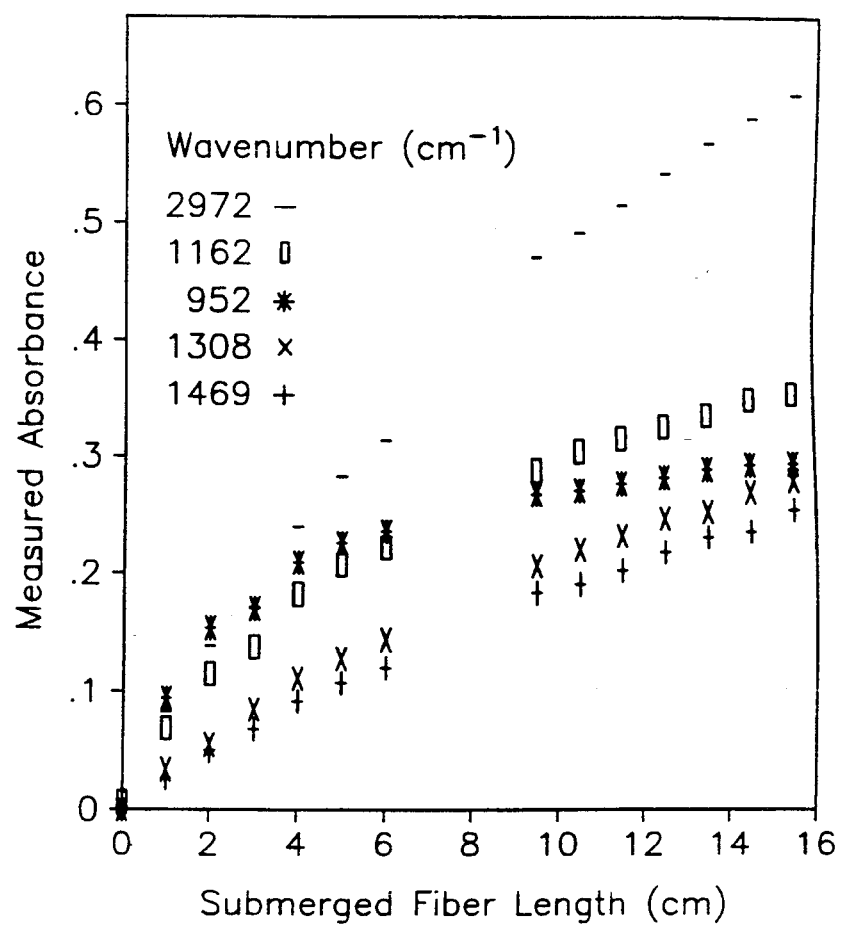
FIG. 11 is a graph illustrating isopropanol absorbance using uncoated fibers of FIG. 9 at five different maximum absorbances using the instant invention.

Using uncoated fiber, the absorption bands of isopropanol are also generally linear as a function of submersion length as long as the absorbance remains below ~0.2 as shown in FIGS. 9 through 11. However, with the large number of bands in this spectrum it is possible to discern a new trend: the onset of nonlinearity is at lower absorbance values for low-frequency than for high-frequency bands. As a result, for example, the intensity of the 951 cm$^{-1}$ band, which is somewhat greater than that of the 2972 cm$^{-1}$ band for a 3-cm submersion length, drops to less than 50% of the latter for a 15.5-cm submersion length. The wavelength dependence of the nonlinearity indicates that the relative mix of effective total path lengths is different at different wavelengths. This is a reflection of different angular distributions of the light intensity in the fiber at different wavelengths.

The isopropanol spectra can be compared with previously-published data using $As_2Se_3$ chalcogenide fiber (See Katz). This has a refractive index (n=2.78) that is similar to the fiber used in the instant disclosures. In Katz, using the $\phi_w$ (wide-angle) launch condition with f/6 mirrors to couple the light from the source into the fiber, the 2971- and 952- cm$^{-1}$ bands exhibited absorbances of 0.05 and 0.11 per cm of submerged fiber (at short lengths). This is roughly comparable to the instant results of 0.08 and 0.09 per cm, respectively shown in FIGS. 9–11. The instant invention employs a thicker fiber than was used in the earlier work (500 vs 300 μm dia.), thereby providing comparable absorbance values using fibers which have a 3-fold-greater cross-sectional area, and correspondingly higher energy throughput capability. The use of a wider range of modes within the fiber thus results in a sensitivity enhancement.

For small values of $\Phi_w$, the measured absorbance is expected to vary as $\sin^2\Phi_w/w$, where w is the fiber diameter (see Katz). As discussed heretofore the value of $\Phi_w$ (the half-angle of the cone of rays being propagated down the fiber is ~51° (using 1 500-μm fiber), as compared to the value of the 10.4° for the prior art (using the 300-μm fiber) (see Katz.)

Figure 12:
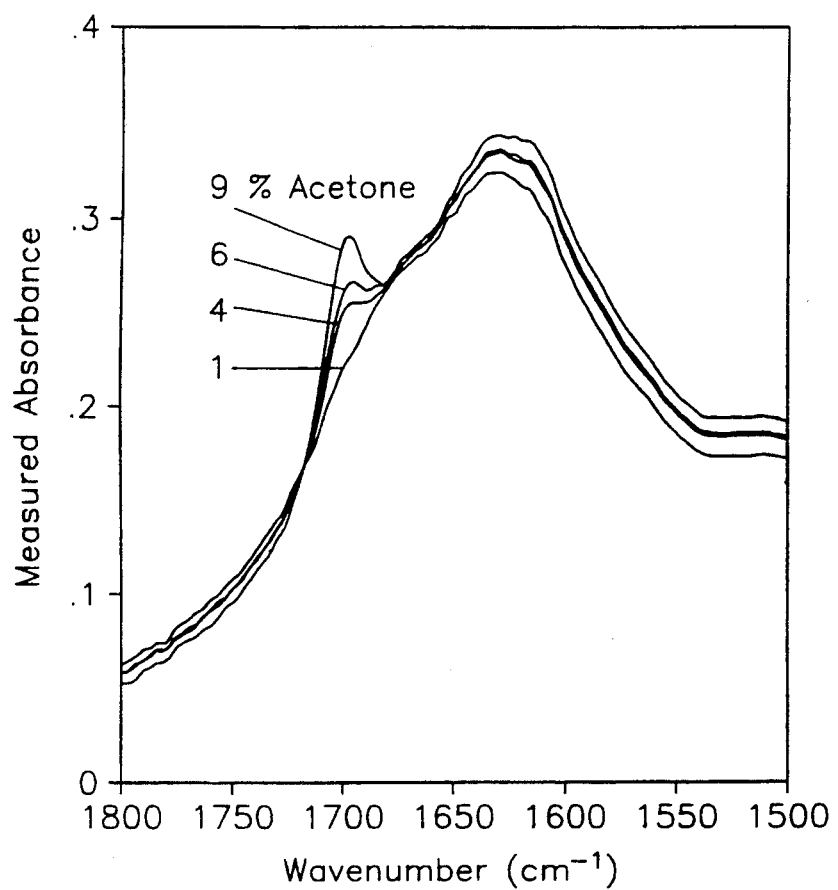
FIG. 12 is a graph illustrating the absorbance spectra of acetone/water mixtures using the instant invention.
Figure 13:
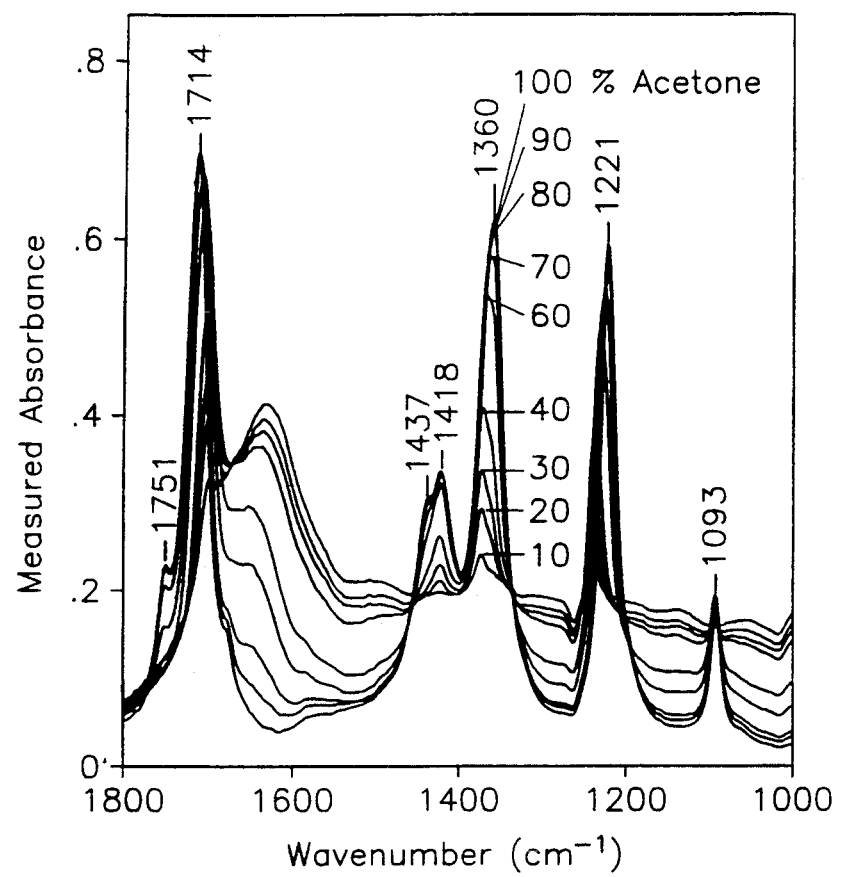
FIG. 13 is an additional graph illustrating the absorbance spectra of acetone/water mixtures using the instant invention.
Figure 14:
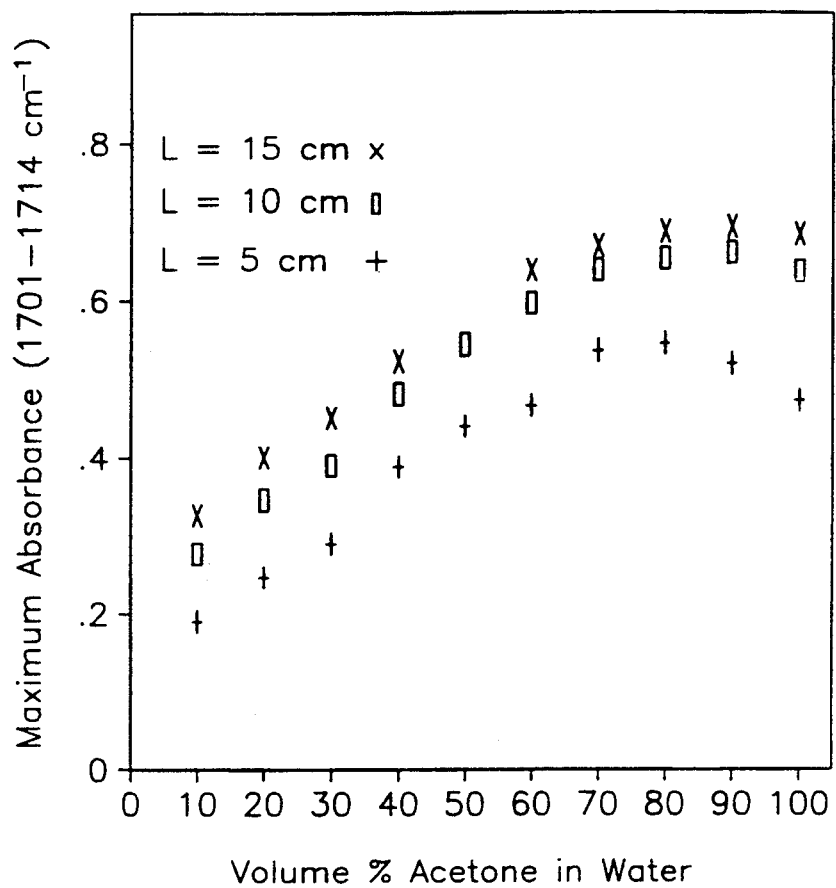
FIG. 14 is a graph illustrating the maximum measured absorbance of a specific peak of acetone vs. water from FIG. 13 using the instant invention.

In FIGS. 12 and 13 an uncoated fiber with a 15-cm submersion length was used to demonstrate the detection of acetone in water, using a dry fiber for the background spectrum. These spectra exhibit sufficiently low noise to detect acetone at concentrations as low as 1% (v/v) in ~1 min. These acetone/water measurements can be compared directly the result of Heo, J., Rodrigues, M., Saggese, S. J. and Sigel, J. G. H (1991) Applied Optics 30, 3944–3951 who used 0.38-mm-dia. $Ge_{27}Se_{18}Te_{55}$ chalcogenide fibers (n≈2.5) and a through-air source-to-fiber coupling based on focusing lenses. The absorbance values of FIG. 12 are a factor of 2–3 higher than those of the prior art. This is despite the use of a 1.3-fold thicker fiber, which would be expected to decrease the number of reflections by the same factor; and the use of a fiber material with a higher refractive index, which would be expected to reduce the penetration depth. The isopropanol spectra of FIGS. 9–11 illustrate that the increased absorbance values with the diamond coupler is that the instant disclosure makes use of high-order modes that are not available using the prior art through-air focusing optics. The higher absorbance values are obtained without any apparent reduction in the throughput of the fiber; enhancing the sensitivity of the fiber as a sensor for low-concentration solutes. For example, the 1701 cm$^{-1}$ acetone band is clearly detectable above the noise in our 1-min spectrum of the 4% mixture as shown in FIG. 12, whereas it is not in the corresponding spectrum of Heo et al.

The sensitivity of the instant disclosure for detecting solutes is also demonstrated in FIG. 15 which shows spectra of low concentrations of glucose in water. These spectra were obtained with plastic-coated fiber. As observed also for the water samples in FIGS. 6 and 8, the evanescent-wave absorbances measured for glucose using the plastic-coated fiber, FIG. 15, were somewhat higher and more linear than those measured with the uncoated fiber (data not shown). This data clearly demonstrate the usefulness of plastic-coated fiber as an evanescent-wave sensor for biologically-important molecules in aqueous solution. With somewhat longer periods of signal averaging, it is possible to use this type of plastic-coated evanescent-wave IR fiber sensor to quantitate glucose at its in vivo concentration of ~0.1%.

Another method for utilizing high-order modes for evanescent-wave spectroscopy is thorough the use of tapered fibers as disclosed in Bornstein, A., Katz, M., Baram, A., and Wolfman, D. (1991) Proc. SPIE 1591, 256–262; Driver, R. D., Downing, J. N. and Leskowitz, F. M. (1991) Proc. SPIE 1591, 168–179. Rays passing through a taper are predicted to become more oblique (i.e., to increase their angle with respect to the fiber axis); thus the narrow cone of rays transmitted into a wide-diameter fiber by a focusing optic can spread out within a tapered region to occupy a cone as large as (or larger than) that produced by the high-index coupling scheme of the instant invention. Within the smallest-diameter portion where the rays are most oblique, they have a large penetration depth. These oblique rays furthermore undergo a very large number of reflections per unit length. These are the same two factors that produce an increase in sensitivity for the diamond-coupled fiber, and so it is useful to compare spectra obtained by the two methods.

Straightforward dimensional modifications of the diamond coupler prototype result in absorbance and throughput results similar to those of any given tapered fiber. However, for some specific applications one method may be preferable over the other. For example, the taper method has a clear advantage for measuring spectral regions where diamond absorbs (~1900–2200 cm$^{-1}$l). On the other hand, use of the diamond coupler avoids the need to manufacture reproducible tapers on the fibers. Fiber replacement is quick, requiring simply the cleaving and reinsertion of commercially-available plastic-coated fibers with standardized diameters. These advantages as well as the source and coupler's small size, weight, and power consumption (compared to other IR source and optical coupling combinations) are like to be most appreciated outside of the traditional research laboratory, e.g. in industrial and clinical settings and for mobile spectrometers in the field.

As discussed in the prior art (Simhony, S., Schnitzer, I., Katzir, A., and Kosower, E. M. (1988) J. Appl. Phys. 64, 3732–3734; Katz, M., Bornstein, A., Schnitzer, I. and Katzir, A. (1991) Proc. SPIE 1591, 236–245; Bornstein, A., Katz, M., Baram, A., and Wolfman, D. (1991) Proc. SPIE 1951, 256–262; Driver, R. D., Downing, N. N. and Leskowitz, G. M. (1991) Proc. SPIE 1591, 168–179) spectra produced by multimode measurements are in general expected to be quite nonlinear. Rays propagating at highly oblique angles will have a much longer effective path length through the surrounding sample that those that are nearly on-axis. As seen in FIG. 11, this mixture of different effective path lengths leads to a spectral flattening effect: as the fiber interaction length or solute concentration is increased, weak absorption bands increase in linear proportion while strong absorption bands grow sublinearly.

While nonlinearity provides a significant limitation on the use of these fibers for quantitative analysis, for other types of spectral analysis the nonlinearity provides significant advantages. One example is that vibrational bands with very different oscillator strengths can be observed using a single set of experimental conditions. For tapered fibers this allowed the observation of vibrational overtone bands in an otherwise normal-appearing spectrum of isopropanol as disclosed in Driver, R. D., Downing, J. N. and Leskowitz, G. M. (1991) Proc. SPIE 1591, 168–179. For example, in the pure acetone spectrum in FIG. 13, the strong band at 1714 cm$^{-1}$ is suppressed somewhat relative to the other features in the spectrum. This allows these other bands to be discerned clearly, without resulting in an off-scale absorbance for the 1714 cm$^{-1}$ band that would obscure its frequency shift that occurs when water is added to the acetone.

A more significant advantage of the nonlinearity is that even when the effective total path length for high-order modes is sufficiently long to produce an absorbance of 3 or 4 for the bulk liquid phase, the low-order modes will not be fully attenuated and can still be used for spectroscopy of materials concentrated right at the surface of the fiber. This effect is used herein in obtaining spectra of single-bilayer membranes coated on the surface of a fiber as disclosed in Braiman, M. S. and Wilson, K. J. (1989), Proc. SPIE 1145, 397–399; Braiman, M. S. and Jonas, R. E. (1992), Proc. SPIE 1796, In Press) demonstrates the advantage of using both low- and high-order modes simultaneously to obtain the spectrum. While the low-order modes are needed to minimize the penetration depth in spectral regions of high water absorbance, simultaneous inclusion of the high-order modes results in improved signal/noise ratios in spectral regions of low background water absorbance. The resulting band-sensitive optimization of signal/noise ration provides a significant advantage that greatly outweighs the loss of linearity in the absolute absorbance scale. This approach is especially useful for highly sensitive difference spectroscopy experiments, where no large absorbance changes are expected to occur in any spectral region.

Finally, ATR spectroscopy in general is expected to result in band intensities that are different from standard transmission-mode spectra. The penetration depth is significantly greater in the lower-wavenumber (longer wavelength) region of the spectrum; as a result relative absorbance values are magnified towards this end of the spectrum as disclosed in Harrick, N.J. (1967) Internal Reflection Spectroscopy (Interscience Publishers-John Wiley and Sons, New York. In FIG. 11, the high nonlinearity in the low-frequency bands results in a decrease in their relative intensity at long interaction lengths, and this decrease effectively cancels the normal ATR enhancement of low-wavenumber peaks. As a result, the isopropanol absorbance spectrum measured with 15.5-cm interaction length shows relative peak heights that are nearly identical with the measure in the transmission mode of FIG. 5 in Katz et al. Thus, for qualitative analysis involving comparisons to a spectral data base obtained in transmission mode, the strong nonlinearities observed with multimode spectroscopy could actually turn out to simplify spectral identifications.

It should be noted that while the preferred embodiment of the invention is described above, numerous alterations of composition or dimensions are possible which would still rely on the same basic features. For example, the diameter of the coupler and fiber could be made smaller or larger, and the lengths of the fiber and diamond coupler could be increased or decreased, although it is preferable that the coupler be a length in the range 1–20 mm. Multiple fibers bundled together could also be substituted for a single fiber.

The invention would also be useful with different fiber materials (such as metal halides or silica glasses) instead of the chalcogenide used in the preferred embodiment. Likewise, the fiber coating could be any flexible material that absorbs light at the measurement wavelengths only weakly and has an index of refraction intermediate between the fiber and the substance whose evanescent-wave absorption spectrum is to be measured; an example would be poly-(tetrafluoroethylene). The source housing could be made out of a different metal than gold-plated copper, as long as its interior surfaces facing the diamond and fiber are highly reflective at the light wavelengths being transmitted, and it is also capable of providing sufficient conductive cooling to protect the fiber from thermal damage.

The source housing could be kept cold by means other than externally-circulating liquid coolant, e.g., by thermoelectric coolers, or by increasing the ratio of surface area to power consumed until air cooling is adequate. The exact dimensions of the housing can also be varied, and it need not be manufactured with any particular number of separate pieces so long as the optical, thermal, and electrical properties described above are present. Also, the atmosphere inside the source housing could be replaced with a low pressure of inert gas at the time of manufacture and the housing sealed, in order to eliminate a need for external tubing on the housing.

The dimensions indicated herein are for reference only and can be altered dependent upon manufacturing and use.

It should be noted that full utilization of the instant invention will depend upon the capabilities of the spectrometer and detector as commercially available units have N.A. values smaller than the fiber. For example, if the field of view of the detector is 40°, corresponding to an N.A. of 0.64, only a subset of the wide cone of rays propagating through the fiber can be brought to focus on the IR detector. Different subsets can be selected by cleaving the output end of the fiber at different angles. The more oblique the cleavage angle, the more light will be collected from high order modes.

Finally, the light source in contact with the diamond coupler need not be a high-emissivity ceramic ("blackbody") radiator. If only limited range(s) of wavelengths need to be transmitted through the optical fiber, this source could be a solid, plastic, or liquid material capable of emitting at specific wavelength(s). This might be, for example, a material which fluoresces when it is heated or illuminated by a laser, or when an external beam of charged particles impinges on it. A material capable of emitting at specific wavelength(s) should be taken to include as well a high-temperature solid-state medium with an optical gain greater than 1 at a particular wavelength(s), for example a photoemissive diode or a glass coupler doped with metal ions, in direct optical contact with the end of the diamond coupler.

What is being claimed is:

1. A light source to optical fiber coupling device comprising, in combination:
   light source means, a diamond coupler, said diamond coupler having a first end and a second end, said diamond coupler having its first end proximate to at least a portion of said light source and optically coupled to said light source, at least one optical fiber, said at least one optical fiber having a first end proximate said second end of said diamond coupler and being in optical coupling relation with said diamond coupler, said first end of said diamond coupler extending into a chamber and being proximate said light source and said second end extending into a passage way.

2. The coupling device of claim 1, wherein said diamond is in the form of a rod.

3. The coupling device of claim 1, further comprising, in combination:
a pair of side housings, each of said pair of side housings having a plurality of sides;
a top housing, said top housing having a plurality of sides and formed of a thermally conductive material;
said pair of side housings adjacent to each other with said top housing above and open space in between;
said chamber having reflective surfaces and being defined by the open space formed between said side housings and top housing
said passage means extending through said top housing, and being coated with a reflective material;
at least a pair of retaining bars, said retaining bars being affixed within said chamber, said light source being retained within said chamber by said retaining bars;
said at least one optical fiber first end extending at least partially into said passage way proximate said diamond coupler.

4. The coupling device of claim 3, wherein said chamber has at least a pair of inlet/outlet ports.

5. The coupling device of claim 3, further comprising a cooling channel, said cooling channel extending through said top housing.

6. The coupling device of claim 3, wherein said conductive material is copper.

7. The coupling device of claim 3, wherein said reflective material is gold.

8. The coupling device of claim 6, wherein said reflective material is gold.

9. The coupling device of claim 3, wherein said retaining bars are contained within said pair of side housings.

10. The coupling device of claim 9, wherein said retaining bars are formed of an electrically conductive material.

11. The coupling device of claim 10, wherein said retaining bars conductive material is platinum.

12. The coupling device of claim 3, further comprising a non-conductive gasket, said non-conductive gasket being between each of said pair of said side housings, thereby insulating said side housings from each other.

13. The coupling device of claim 3, further comprising non-conductive gaskets, said non-conductive gaskets being between said top housing and said pair of side housings, thereby insulating said top housing from said pair of side housings.

14. The coupling device of claim 1, wherein said diamond coupler is a natural diamond.

15. The coupling device of claim 1, wherein said diamond coupler is a synthetic diamond.

16. The coupling device of claim 1, wherein said light source is a broadband light source.

17. The coupling device of claim 1, wherein said light source is a narrowband light source.

18. The coupling device of claim 1, wherein said light source is infrared radiation.

19. The coupling device of claim 1, further comprising light regulating means, said light regulating means maintaining said light source at a desired constant temperature between 0 and 2000 degrees Kelvin, and consequent constant luminance.

20. The coupling device of claim 1, further comprising a diamond plate, said diamond plate being positioned between said diamond coupler and said light source.

21. The coupling device of claim 3, wherein said reflective surfaces of said passage means enable efficient transmission into the fiber of light rays traveling at angles greater than 58 degrees from the fiber axis by reflecting said light rays within said diamond coupler until it reaches said at least one optical fiber.

22. A light source to optical fiber coupling device comprising, in combination:
a light source for emitting light,
a diamond optical coupler, said diamond coupler being rod shaped, having a first end and a second end,
said diamond optical coupler having its first end proximate said light source and optically coupled with said light source to transmit light emitted from said light source;
at least one optical fiber, said at least one optical fiber having a first end proximate the second end of said diamond coupler, positioned so as to be optically coupled to said diamond coupler in order to receive light transmitted through said diamond optical coupler emitted by said light source.

23. The coupling device of claim 22 wherein:
the diamond optical coupler has a length of 1–20 mm.

24. The coupling device of claim 22 wherein:
the at least one optical fiber is in a fluid.

25. The coupling device of claim 22 wherein:
said at least one optical fiber is a chalcogenide fiber.

26. The coupling device of claim 22, wherein:
said light source is a broadband light source;
said light source and the first end of said diamond coupler are separated by a distance less than the shortest wavelength of light coupled into said at least one optical fiber.

27. The coupling device of claim 26, wherein:
said light source has a temperature of over 1100° K.

28. The coupling device of claim 22, further comprising, in combination:
a chamber at least partially surrounded by a reflective wall;
a passage way, at least one end of which is said chamber, and the inner surface of which is reflective;
said light source and the first end of said diamond optical coupler being located in said chamber;
the second end of said diamond optical coupler and the first end of said at least one optical fiber being located in said passage way, such that light emitted by said light source entering the diamond optical coupler at an angle greater then the angle of total internal reflection of the diamond coupler is reflected from the inner surface of said passage way and coupled into said at least one optical fiber.

29. The coupling device of claim 28, further comprising, in combination:
said chamber comprising:
a pair of side housings, each of said pair of side housings having a plurality of sides,
a top housing, said top housing having a plurality of sides and formed of a thermally conductive material,
said pair of side housings adjacent to each other with said top housing above and an area in-between;
said chamber having reflective surfaces and defined by the area between said side housings and top housing;
said passage means extending through said top housing, and being coated with a reflective material;
at least a pair of retaining bars, said retaining bars being affixed within said chamber, said light source being retained within said chamber by said retaining bars;
said at least one optical fiber first end extending at least partially into said passage way proximate said diamond optical coupler.

30. The method of minimizing refraction loss in optical spectroscopy using a light source to optical fiber coupling device comprising, in combination:
light source means,
diamond coupler, said diamond coupler having a first end and a second end, said diamond coupler having its first end proximate to said light source and optical coupled with said light source,
at least one optical fiber, said at least one optical fiber having a first end proximate said second end of said diamond coupler and being in optical coupling relation with said diamond coupler,
said diamond coupler having a first end and a second end, said first end extending into a chamber and being proximate said light source and said second end extending into a passage way; comprising the steps of
activating a power source and thereby causing light to emanate from a light source;
transmitting said generated light from said light source, through a diamond optical coupler to at least one optical fiber, thereby enabling efficient, simultaneous transmission into the optical fiber of light rays that travel within the fiber at angles ranging from 0 degrees to greater than 58 degrees from the fiber axis.

31. The method of claim 30, further comprising cooling said light source thereby maintaining it within predetermined temperature.

32. The method of minimizing refraction loss in optical spectroscopy comprising the steps of:
activating a power source and thereby causing light to emanate from a light source;
transmitting said generated light from said light source, through a diamond optical coupler to at least one optical fiber, thereby enabling efficient transmission into the optical fiber of light rays traveling at angles ranging greater than 58 degrees from the fiber axis, wherein said optical fiber has a plastic coating of from about 10 to about 400 micron thickness, further comprising the step of obtaining evanescent-wave absorption spectra of liquid containing samples in contact with said coated optical fiber.

33. The method of claim 32, wherein said diamond coupler is within a chamber, said chamber being, said chamber having reflective gold coated surfaces, and comprising reflecting light from said gold coated surfaces to said optical fiber.

34. The method of claim 32 wherein said liquid is water.

35. The method of claim 32, wherein said coating material is polytetrafluoroethylene.

* * * * *